(12) United States Patent
Coughlin et al.

(10) Patent No.: US 9,974,537 B2
(45) Date of Patent: May 22, 2018

(54) INSTRUMENTS AND METHODS FOR COMPLETE PLANTAR PLATE REPAIRS

(71) Applicants: ARTHREX, INC., Naples, FL (US); Jennifer E. Shurnas

(72) Inventors: Michael J. Coughlin, Boise, ID (US); Lowell F. Weil, Jr., Des Plaines, IL (US); Paul S. Shurnas, Lafayette, CO (US); Jesse G. Moore, Frisco, TX (US); William Michael Karnes, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days. days.

(21) Appl. No.: 15/437,079

(22) Filed: Feb. 20, 2017

(65) Prior Publication Data
US 2017/0156721 A1     Jun. 8, 2017

Related U.S. Application Data

(63) Continuation of application No. 13/724,600, filed on Dec. 21, 2012.
(Continued)

(51) Int. Cl.
*A61B 17/02* (2006.01)
*A61B 17/04* (2006.01)
(Continued)

(52) U.S. Cl.
CPC ........ *A61B 17/0469* (2013.01); *A61B 17/025* (2013.01); *A61B 17/0206* (2013.01);
(Continued)

(58) Field of Classification Search
CPC . A61B 17/60; A61B 17/0861; A61B 17/8866; A61B 17/8897; A61B 2017/047;
(Continued)

(56) References Cited

U.S. PATENT DOCUMENTS 5,586,564 A   12/1996  Barrett et al.
5,681,333 A   10/1997  Burkhart et al.
(Continued)

FOREIGN PATENT DOCUMENTS

GB         2198647 A  *  6/1988  ........... A61B 17/025

OTHER PUBLICATIONS

AO Surgery. Collateral Ligament Repair. Aug. 11, 2008.*
(Continued)

*Primary Examiner* — Thomas J Sweet
*Assistant Examiner* — Christie Bahena
(74) *Attorney, Agent, or Firm* — Carlson, Gaskey & Olds

(57) ABSTRACT

Surgical repair systems and techniques for plantar plate repairs. The surgical repair systems and methods reconstruct the plantar plate through a dorsal incision. The surgical repair system embodies a variety of instruments that provide visualization and access to the plantar plate using suture to complete the repair. The repair system may include some or all of the following instruments: a metatarsal head pusher employed in open surgical space, to move the "capital fragment" in a controlled manner; a suture retriever instrument and a suture retriever funnel (sleeve); a suture passer such as a Mini Scorpion DX and accompanying needle, or a variety of shaped Micro Suture Lassos; a measuring guide; and a small joint distractor.

16 Claims, 26 Drawing Sheets

Related U.S. Application Data

(60) Provisional application No. 61/583,915, filed on Jan. 6, 2012.

(51) Int. Cl.
    *A61B 90/00*         (2016.01)
    *A61B 17/00*         (2006.01)
    *A61F 2/42*          (2006.01)

(52) U.S. Cl.
    CPC .......... *A61B 17/0485* (2013.01); *A61B 90/06* (2016.02); *A61B 2017/0023* (2013.01); *A61B 2090/061* (2016.02); *A61F 2/4225* (2013.01); *A61F 2002/4233* (2013.01); *A61F 2002/4235* (2013.01)

(58) Field of Classification Search
    CPC ................. A61F 2/0811; A61F 2/4606; A61F 2002/0882; A61F 2002/0817; A61F 2002/0823; A61F 2002/0829; A61F 2002/0835; A61F 2002/0841; A61F 2002/0847; A61F 2002/0858; A61F 2002/0864; A61F 2002/087; A61F 2002/0876; A61F 2002/0888; A61F 2002/0894; A61F 2002/4212; A61F 2002/42

See application file for complete search history.

(56) References Cited

U.S. PATENT DOCUMENTS

| | | | |
|---|---|---|---|
| 6,533,795 | B1 | 3/2003 | Tran et al. |
| 6,716,234 | B2 | 4/2004 | Grafton et al. |
| 2004/0147935 | A1 | 7/2004 | Segler |
| 2009/0187080 | A1* | 7/2009 | Seex .................... A61B 17/02 600/210 |
| 2010/0130990 | A1 | 5/2010 | Saliman |
| 2011/0264149 | A1* | 10/2011 | Pappalardo ........ A61B 17/8019 606/286 |
| 2011/0288595 | A1* | 11/2011 | Niederberger ..... A61B 17/8019 606/286 |
| 2013/0184818 | A1 | 7/2013 | Coughlin et al. |

OTHER PUBLICATIONS

Cusumano, Thomas, DPM. Restoring the Metatarsal Parabola with the Weil Osteotomy. Podiatry Today. vol. 15, Issue 7, Jul. 2002.*
Segler 1-4, Segler Ligament Release. Segler, Christopher. Tarsal Joint Distractor Video. Dec. 8, 2009. Tarsal Joint Distractor Facebook Page.*
Weil. Weil Foot and Ankle website. Accessed Apr. 30, 2015.
Re, Louis Peter: Double Row Rotator Cuff Repair using Novel 'Inverted Mattress' OPUS Technique. Copyright 2007. ArthroCare Sports Medicine.
Gregg, Julie, et al: Plantar plate repair and Weil osteotomy for metatarsophalangeal joint instability. Foot and Ankle Surgery 13 (2007). 116-121.
Coughlin, Michael, et al; Second MTP Joint Instability: Grading of the Deformity and Description of Surgical Repair of Capsular Insufficiency; The Physician and Sportsmedicine, vol. 39, Issue 3, Sep. 2011. pp. 132-141.
Blitz, Neal, et al; Plantar Plate Repair of the Second Metatarsophalangeal Joint: Technique and Tips; 2004. The Journal of Foot & Ankle Surgery. pp. 266-270.
Weil, Lowell, et al; Current Concepts in Plantar Plate Repair; Podiatry Today, weil4feet.com. 2012.
L. Weil Jr., et al; Weil Metatarsal Osteotomy: Introducing New Technique for Plantar Plate Repair; 3rd Joint Meeting of International Federation of Foot & Ankle Societies, Weil Foot & Ankle Institute, Sep. 2008, with abstract.
E. Klein et al; The Underlying Osseous Deformity in Plantar Plate Tears, A Radiographic Analysis, Foot and Ankle Specialist, vol. 8, No. 2, Apr. 2013, pp. 108-117.
L. Weil, Jr., et al; Anatomic Plantar Plate Repair Using the Weil Metatarsal Osteotomy Approach, Foot & Ankle Specialist, vol. 4, No. 3, Jun. 2011, pp. 145-150.
E. Klein, et al; Clinical Examination of Plantar Plate Abnormality: A Diagnostic Perspective, Foot and Ankle International 34 (6), pp. 800-804.
E. Klein, et al; Magnetic Resonance Imaging Versus Musculoskeletal Ultrasound for Identification and Localization of Plantar Plate Tears, Weil Foot & Ankle Institute, Des Plaines, Illinois, www.weil4feet.com.
E. Klein, et al; Musculoskeletal Ultrasound for Preoperative Imaging of the Plantar Plate: A Prospective Analysis, Foot and Ankle Specialist, vol. 8, No. 3, Jun. 2013, pp. 196-200.

* cited by examiner

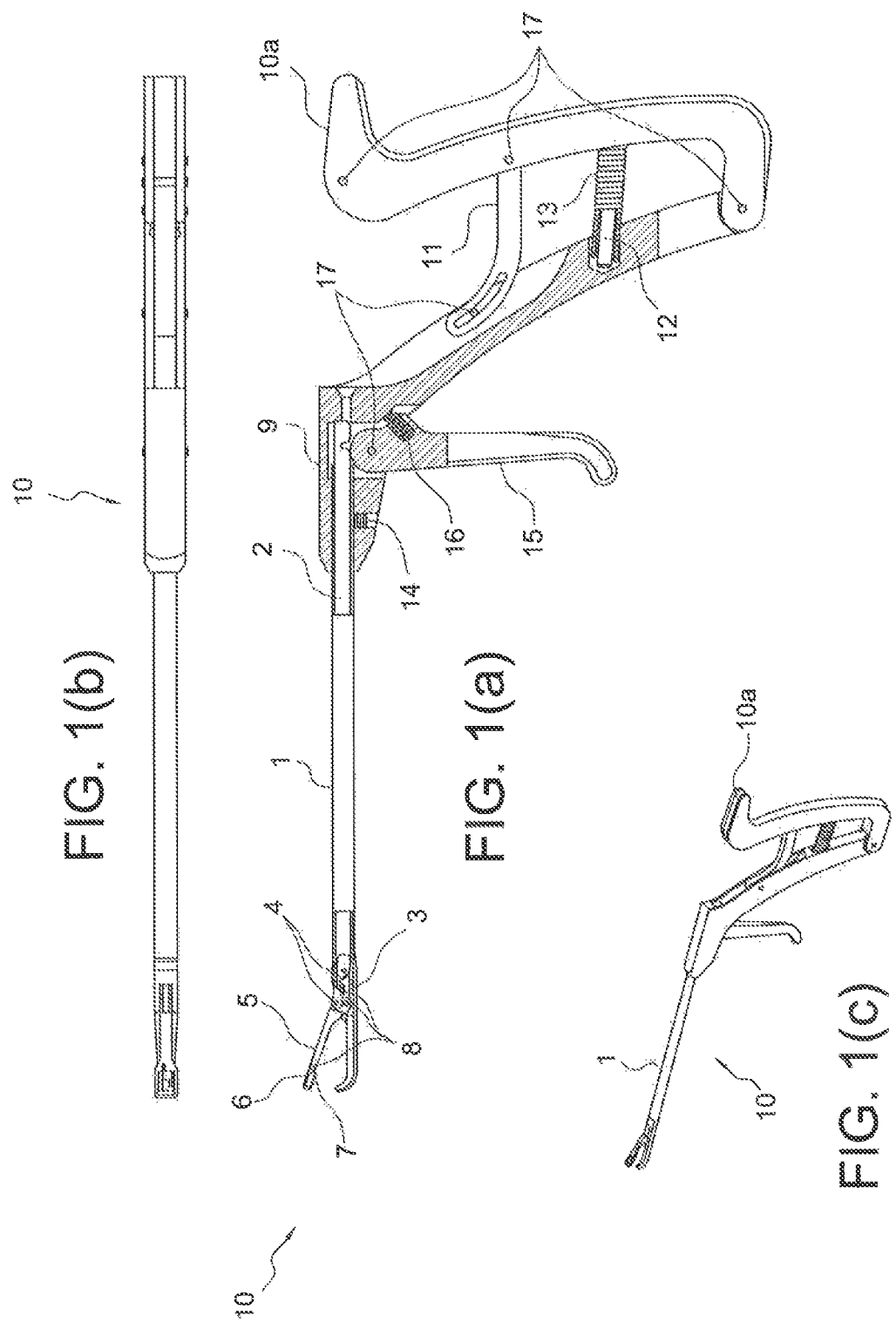

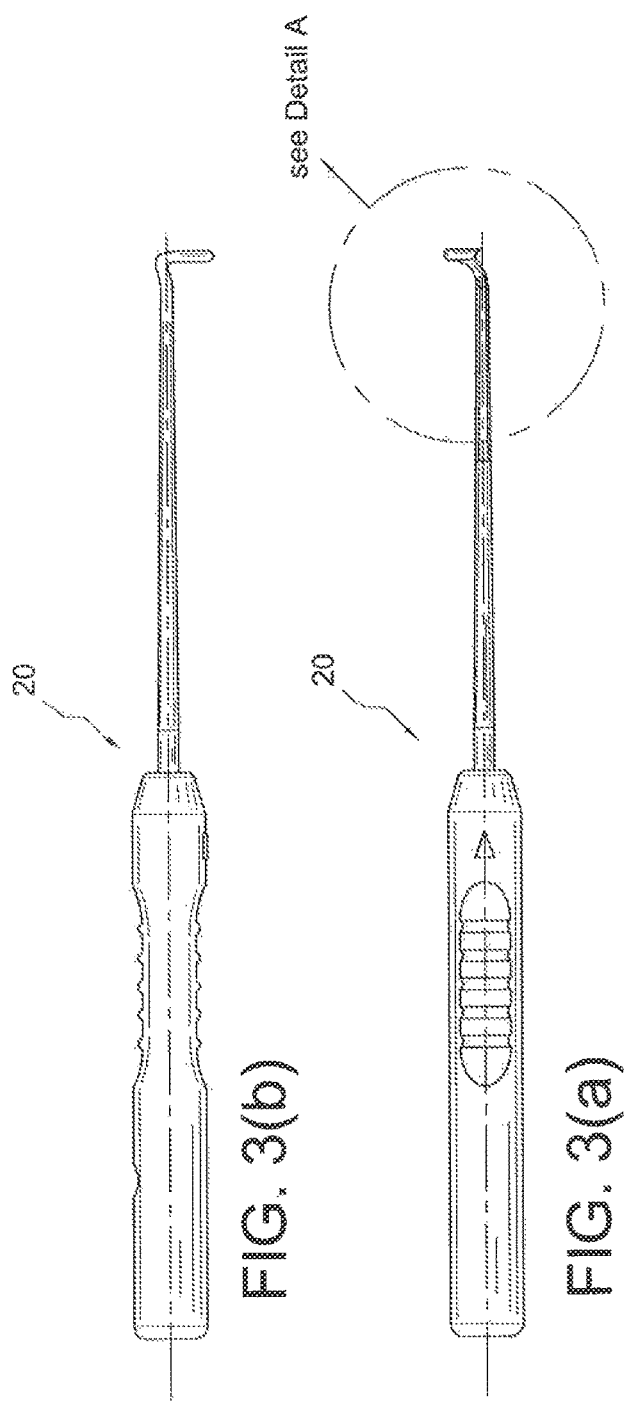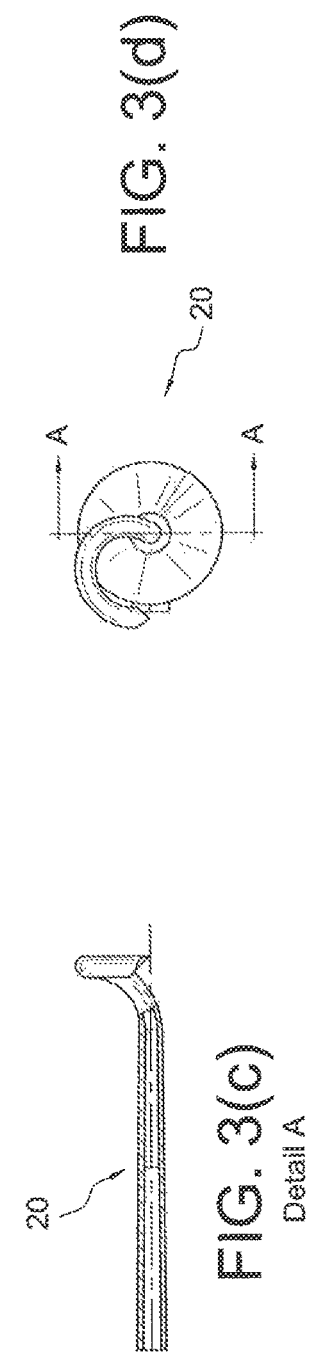

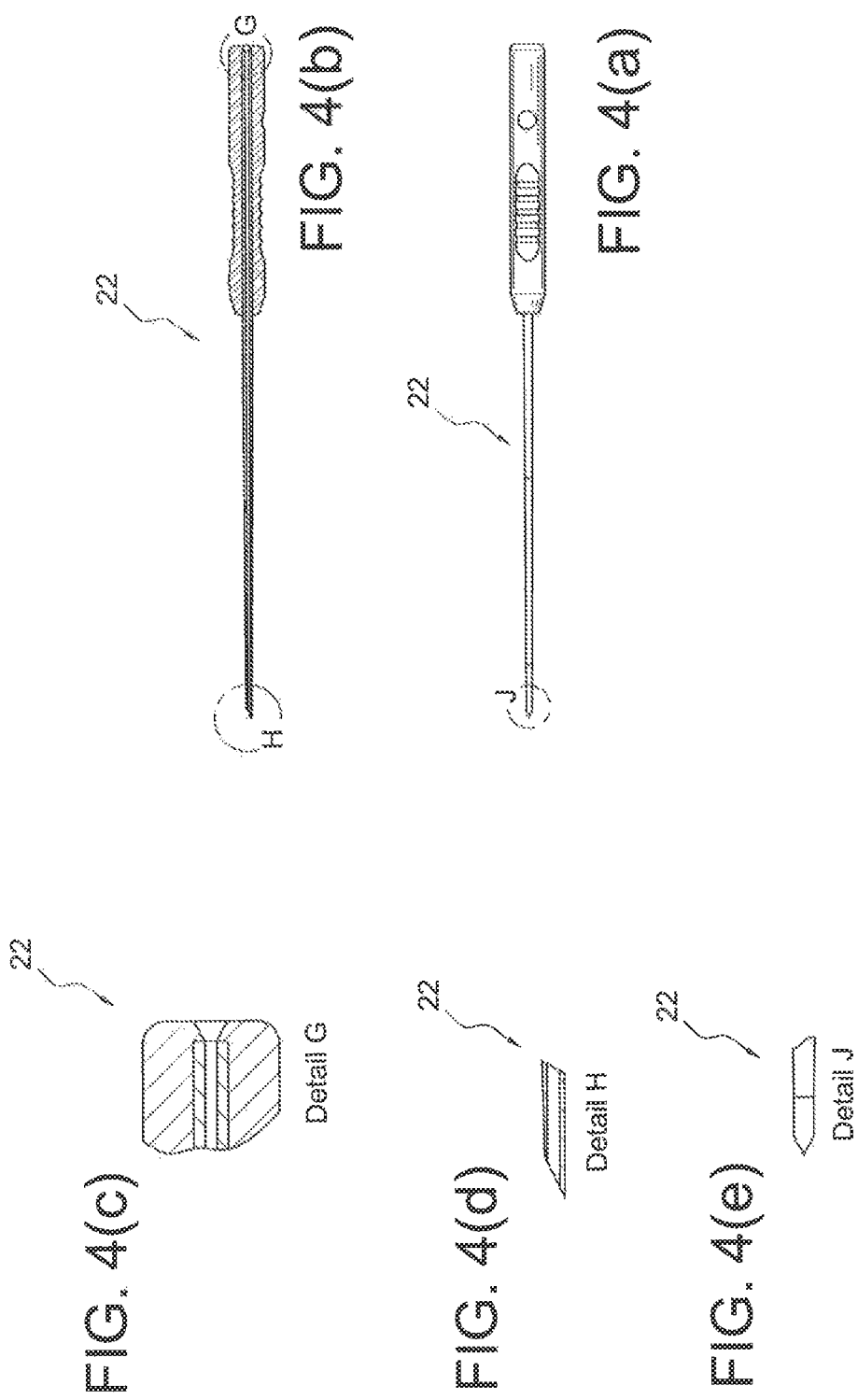

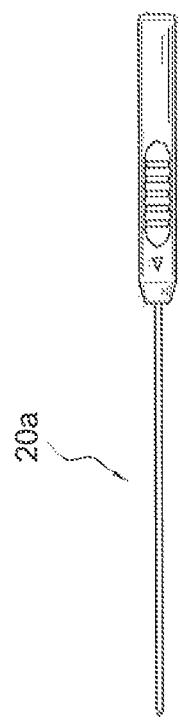
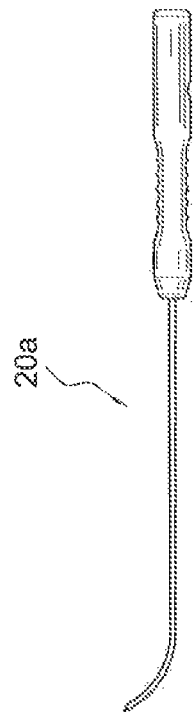
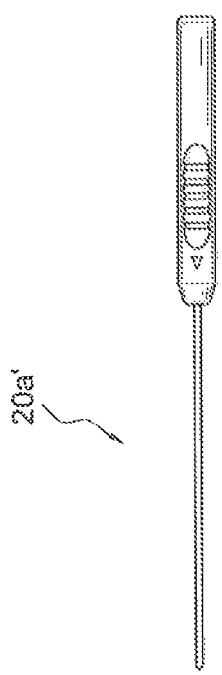
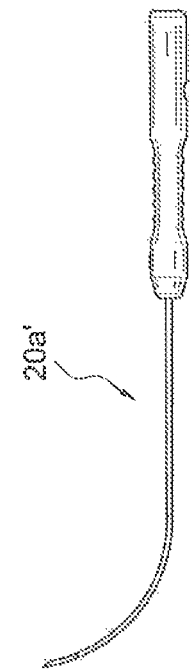

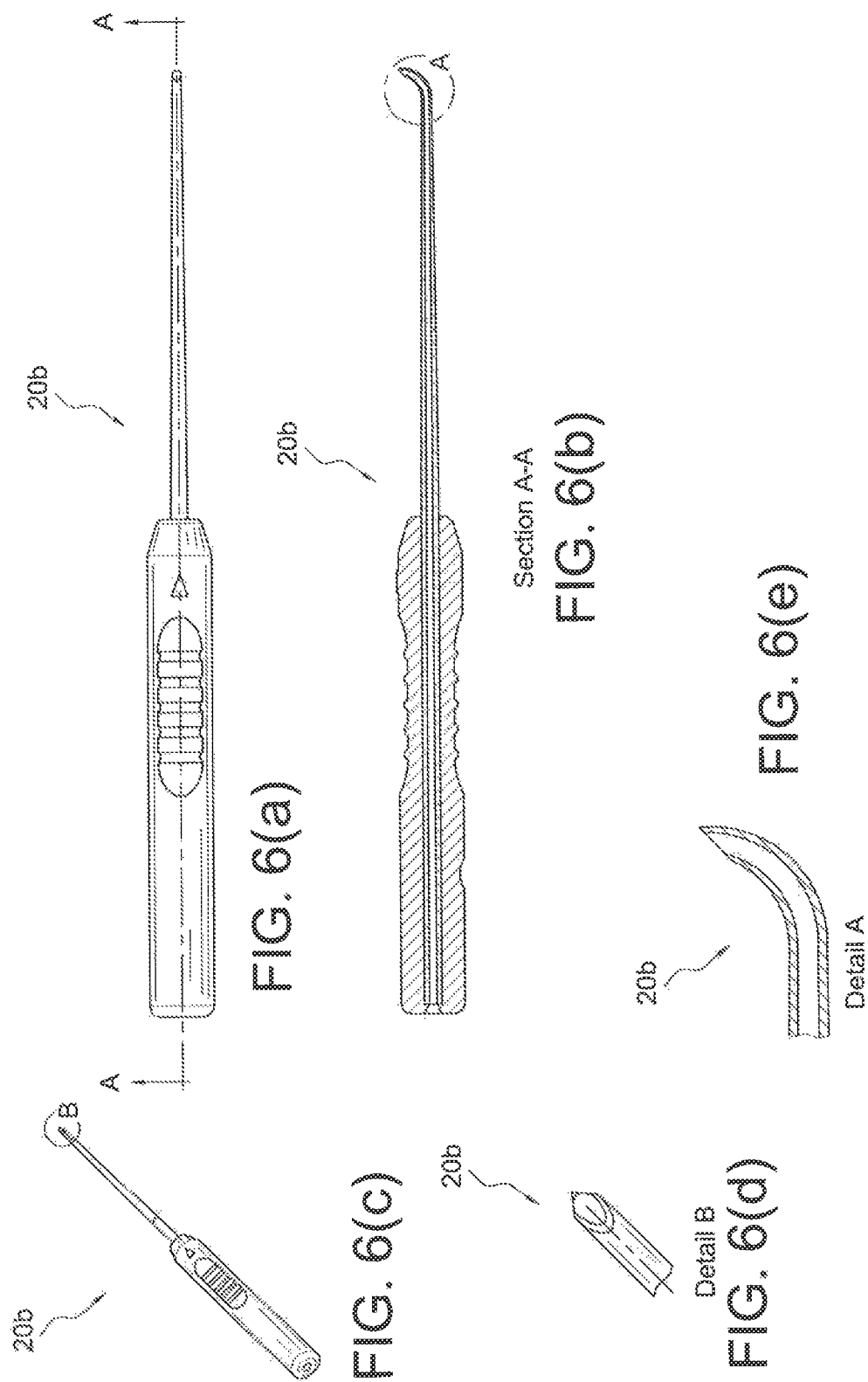

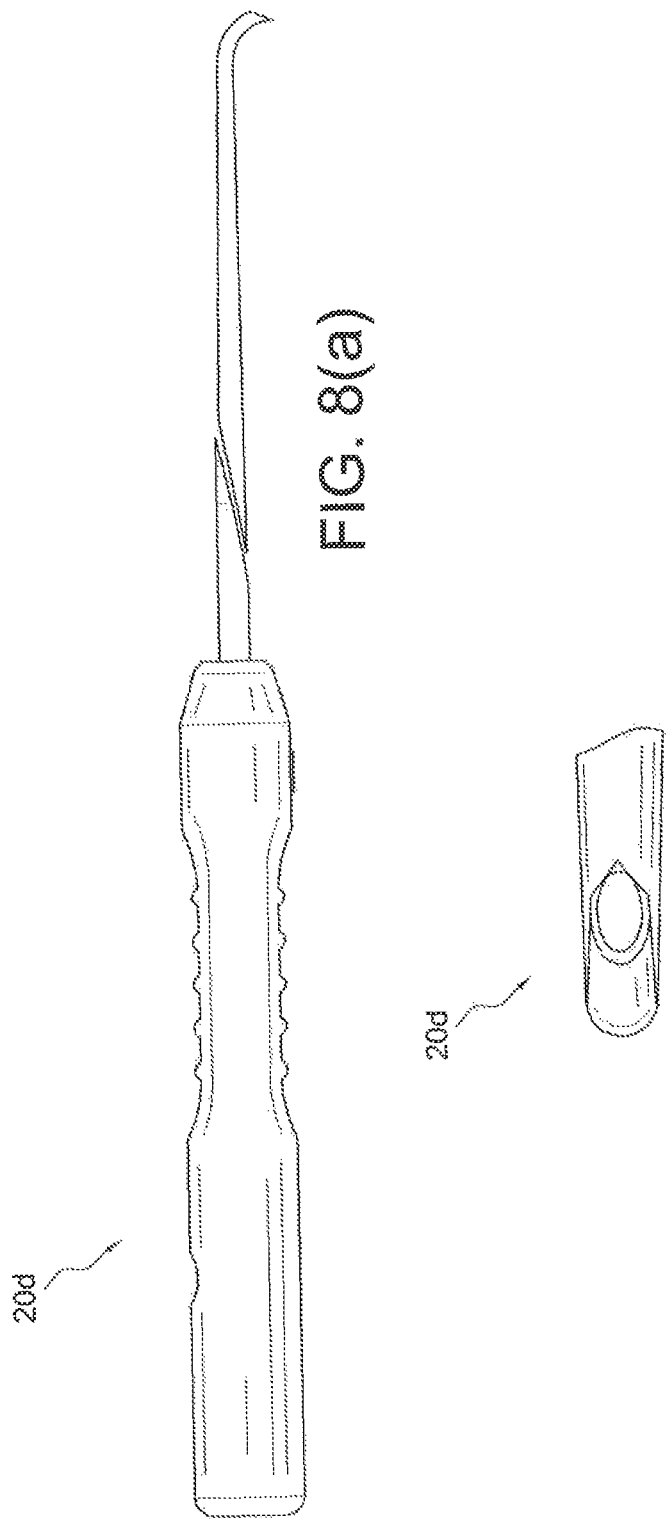

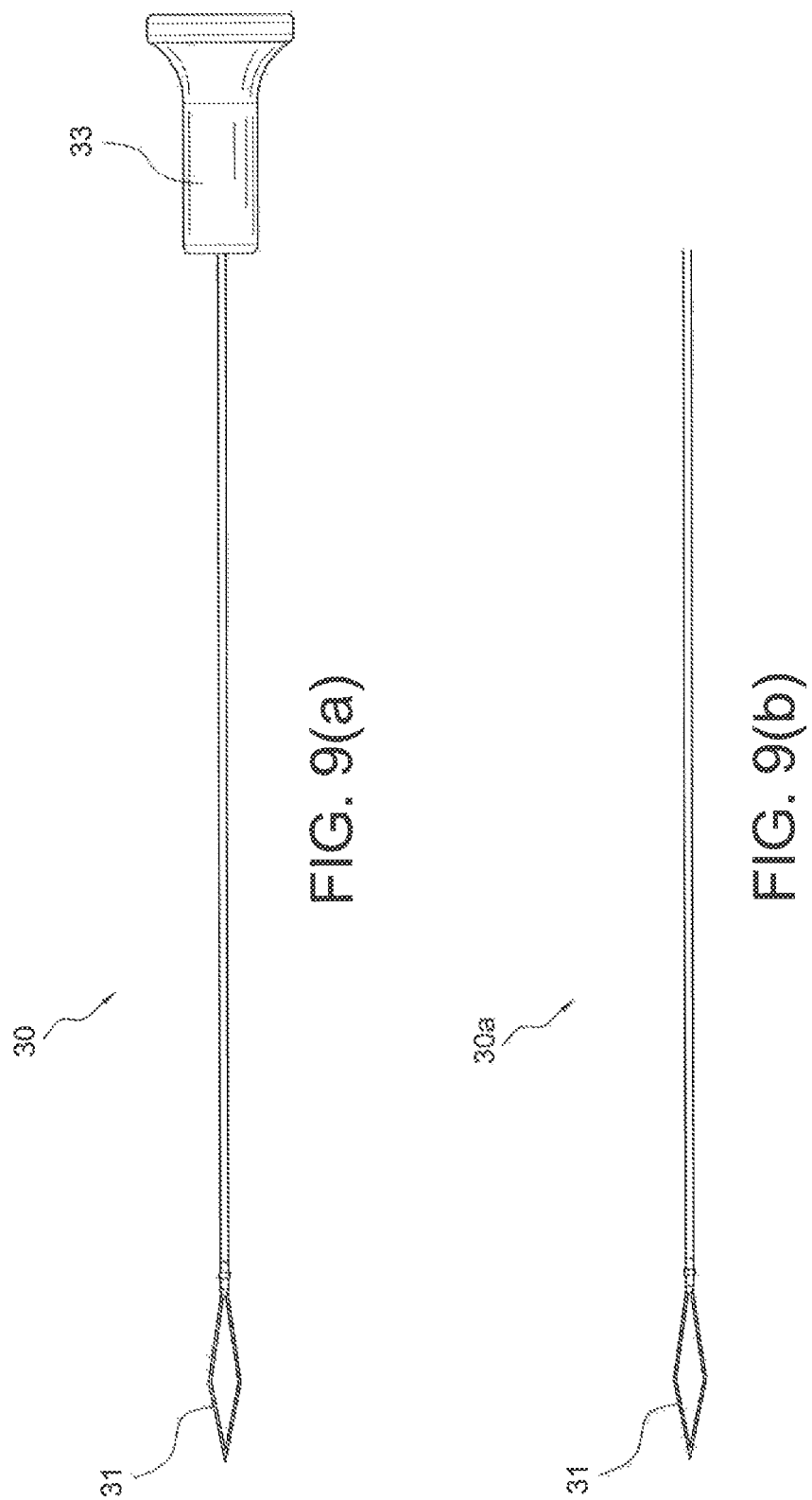

Section A-A

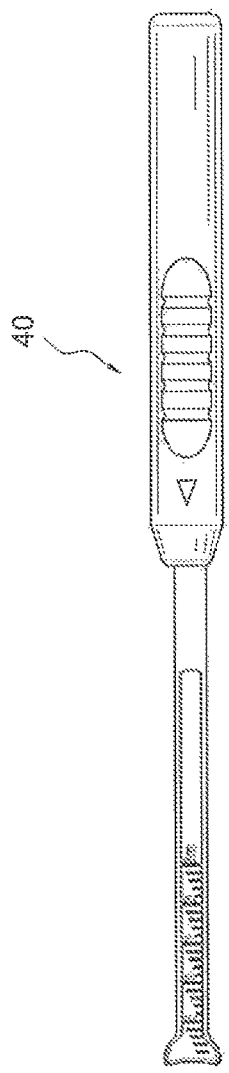
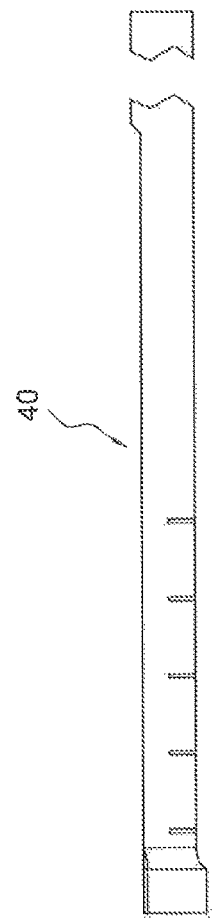
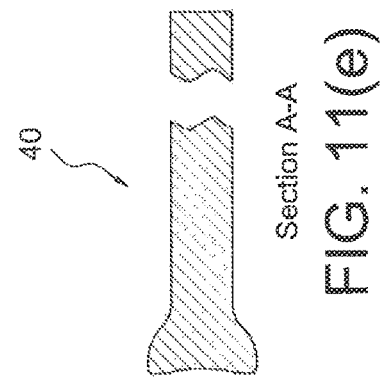
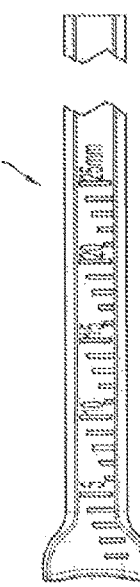
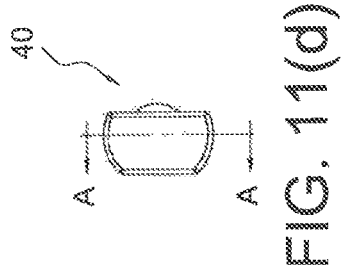
FIG. 11(a)
FIG. 11(b)
FIG. 11(c)
FIG. 11(d)
FIG. 11(e) Section A-A

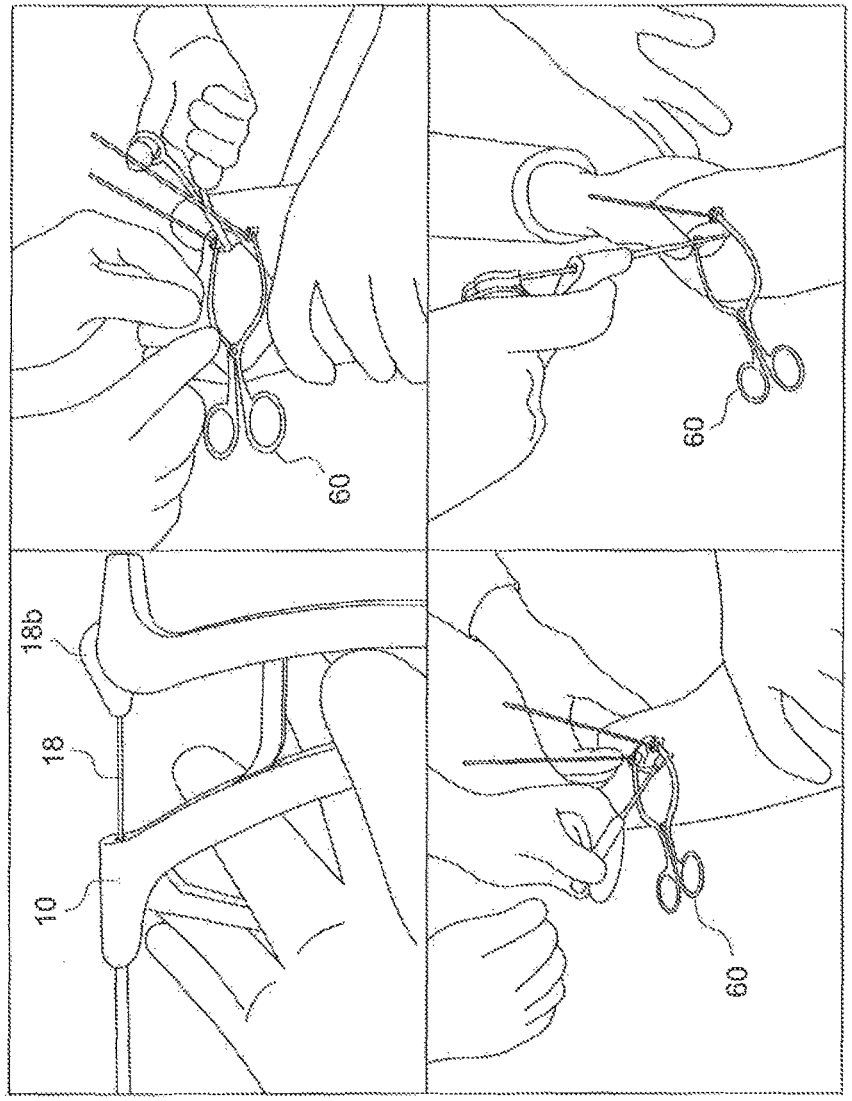

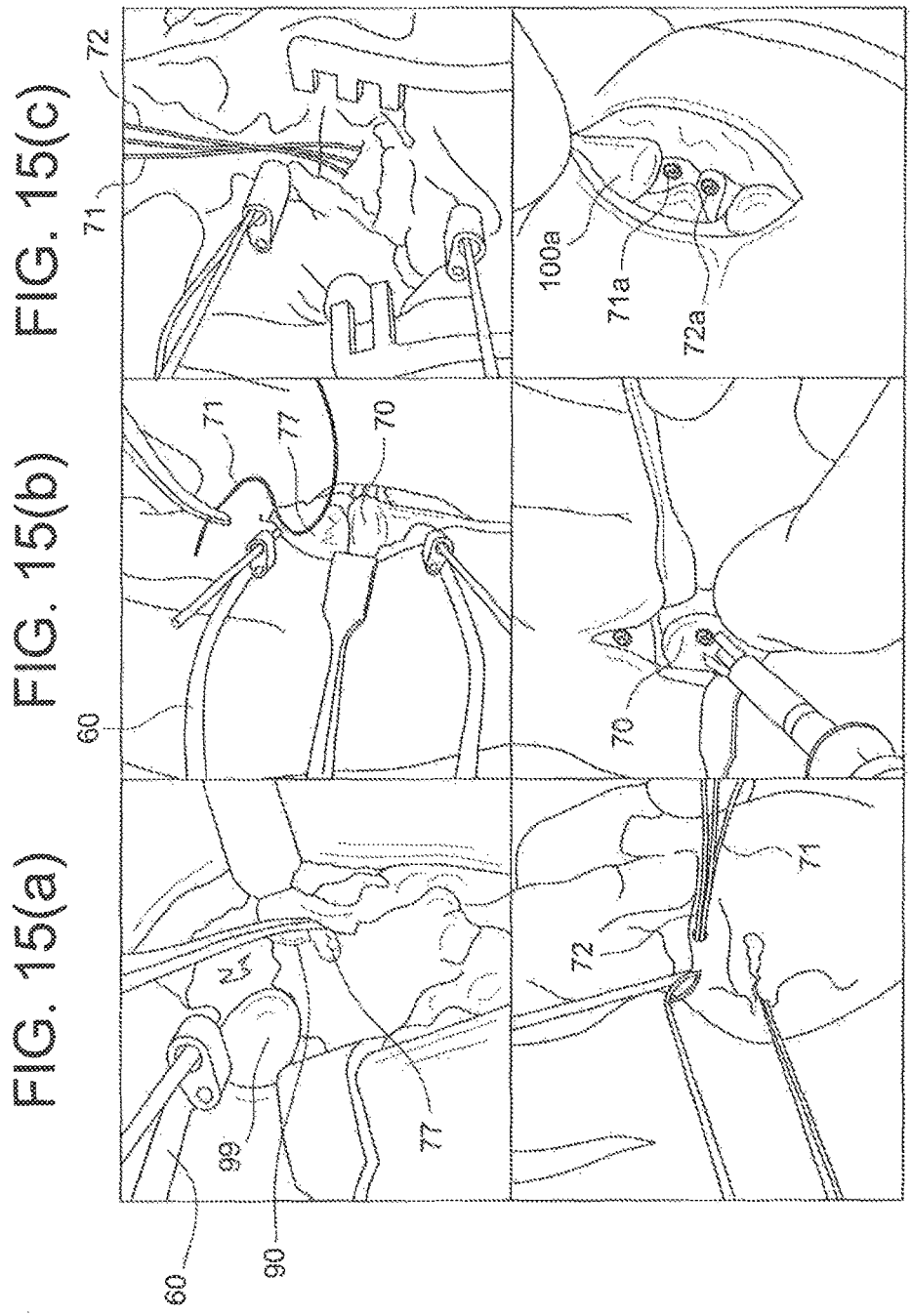

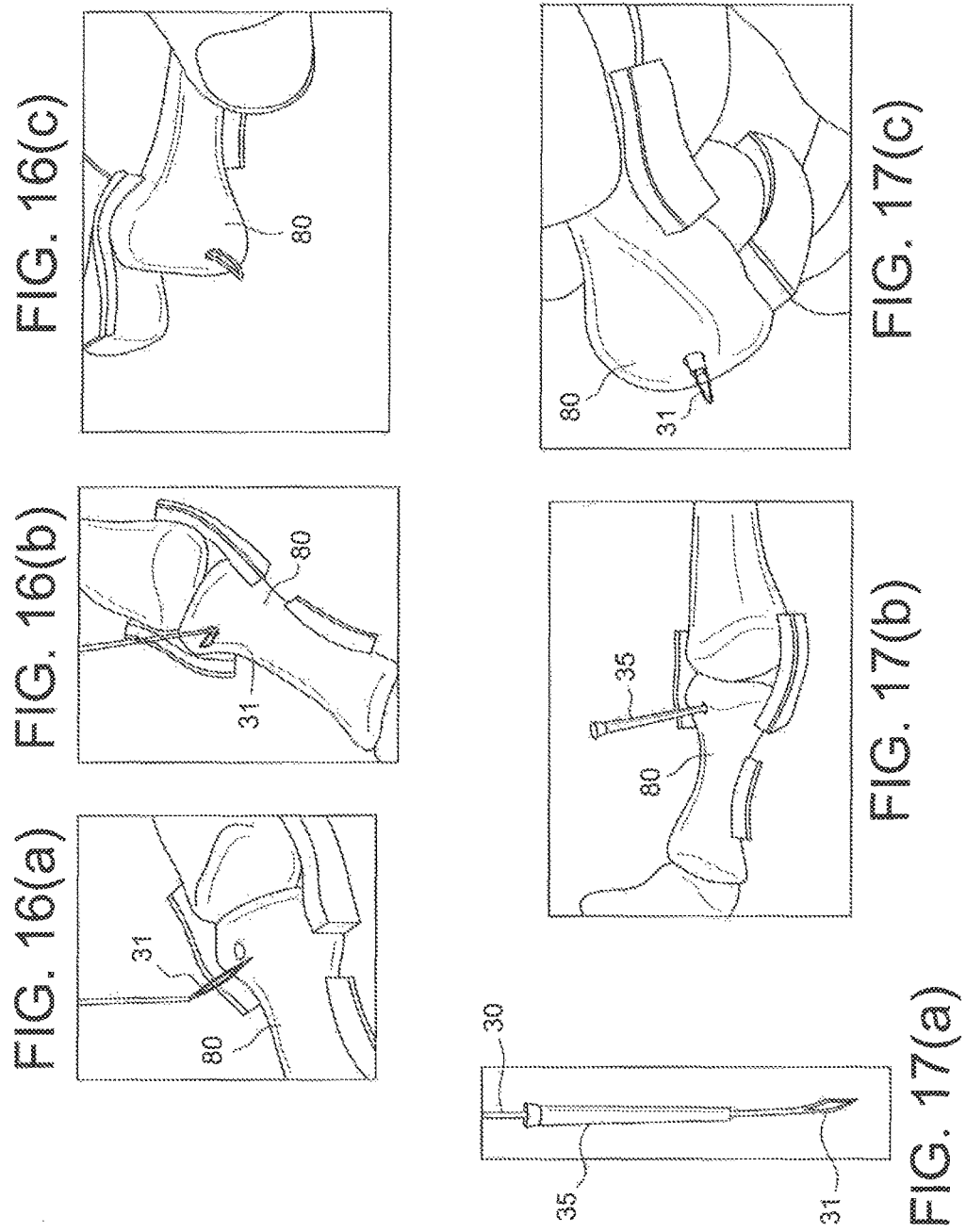

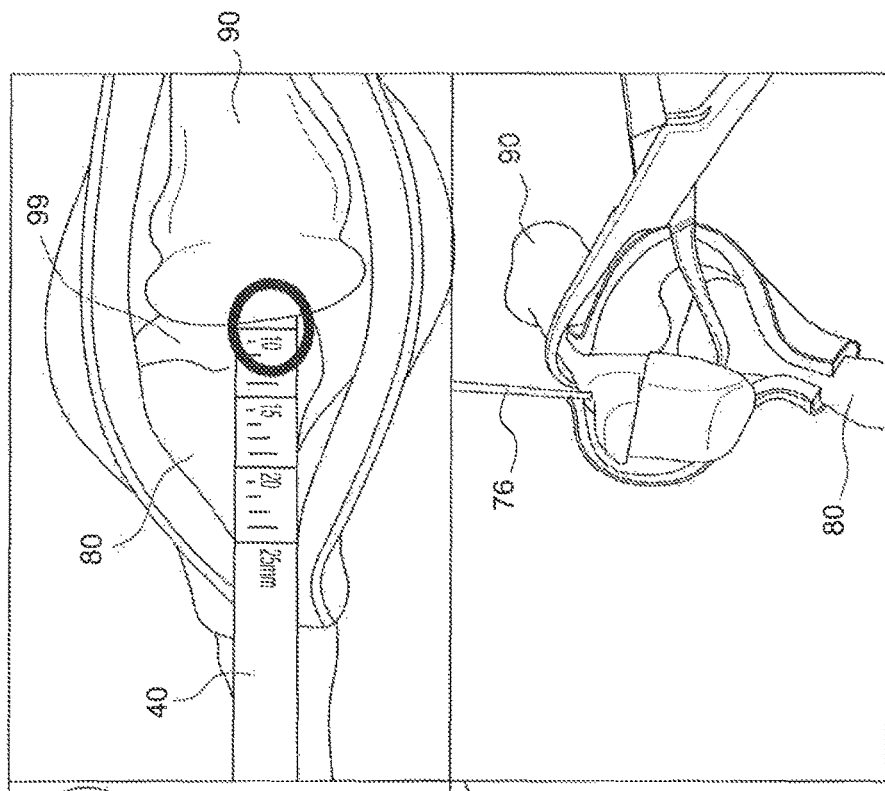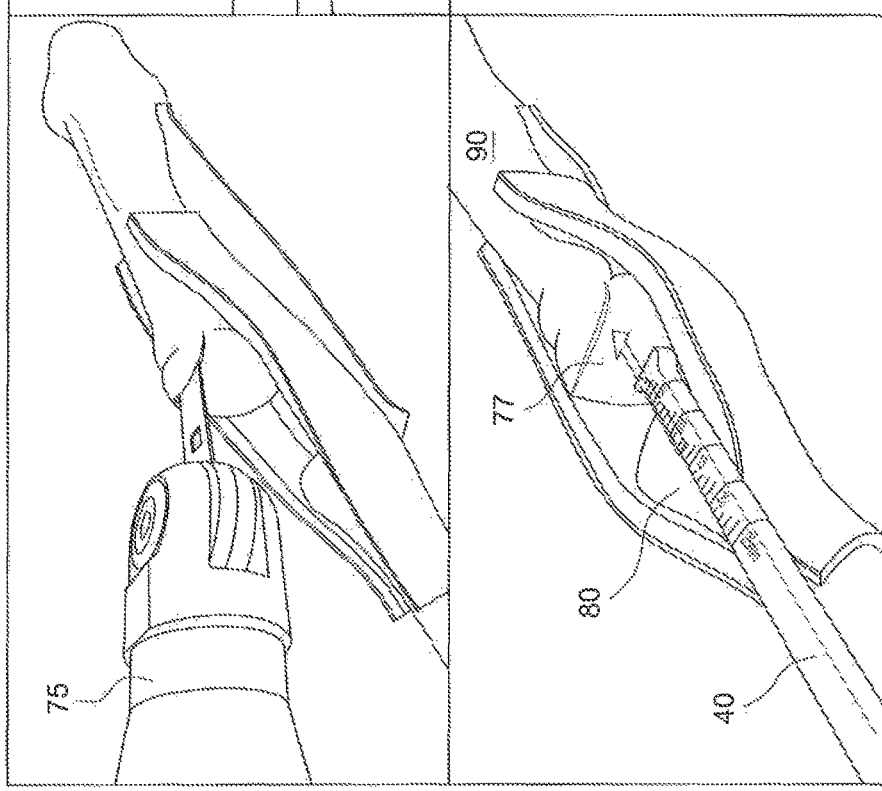

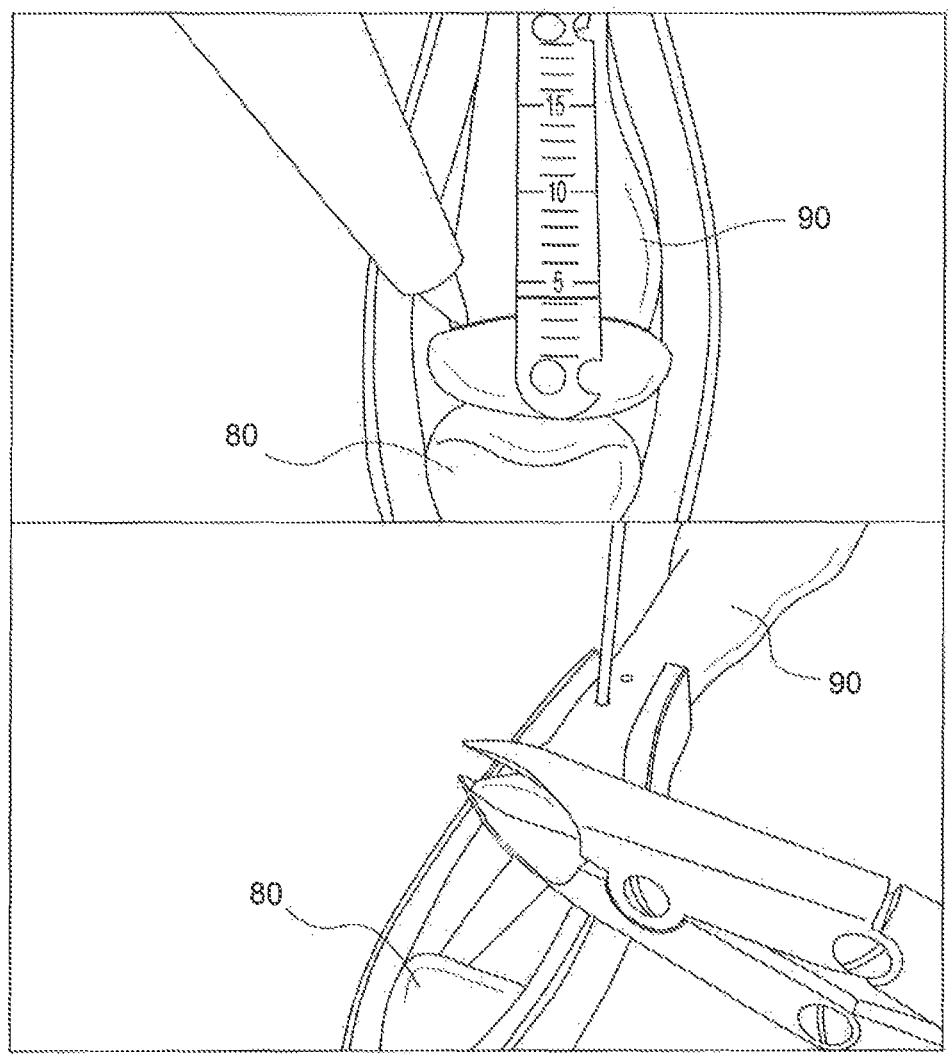

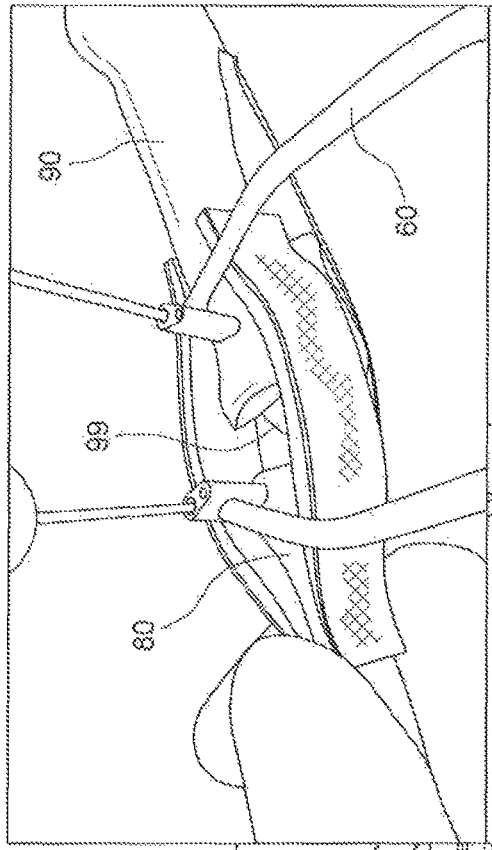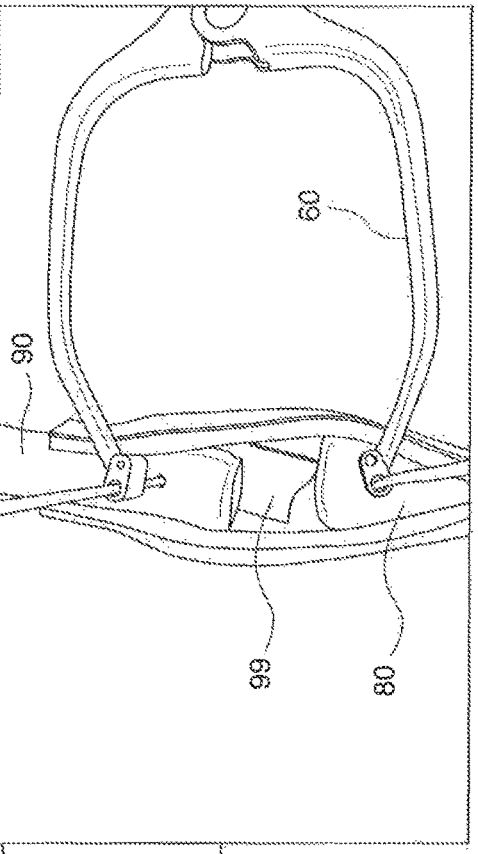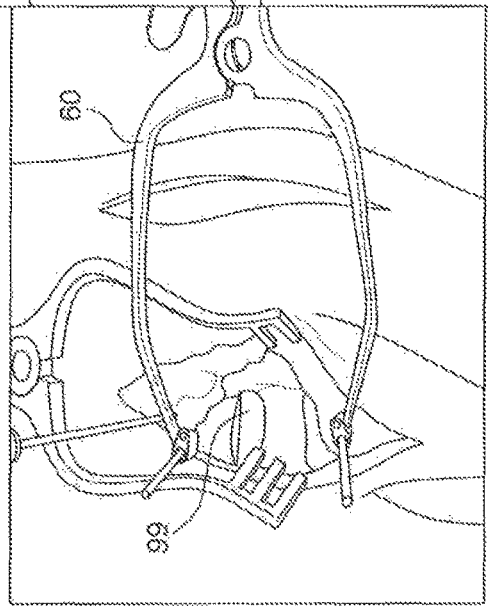

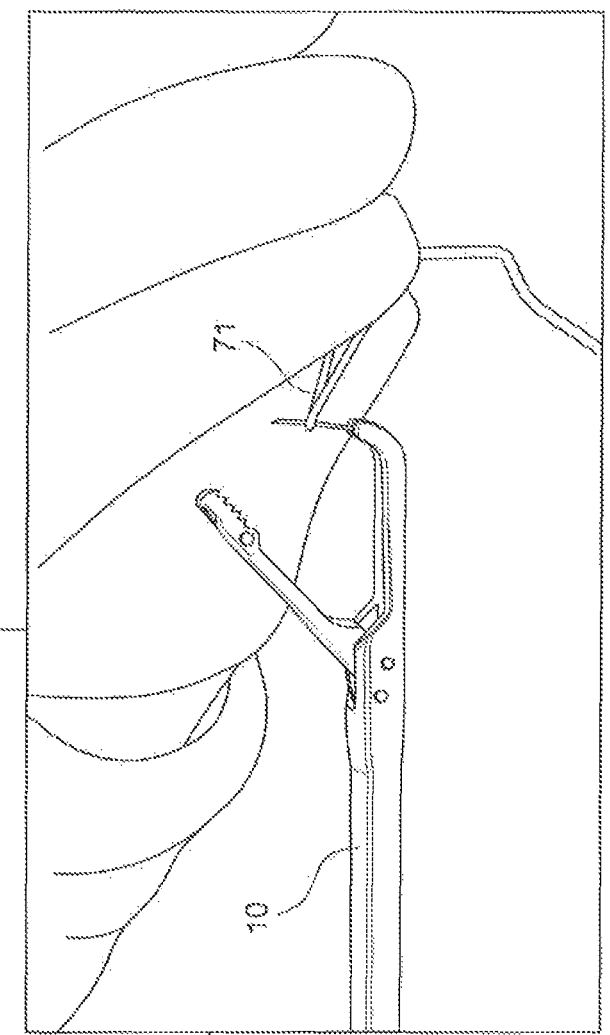
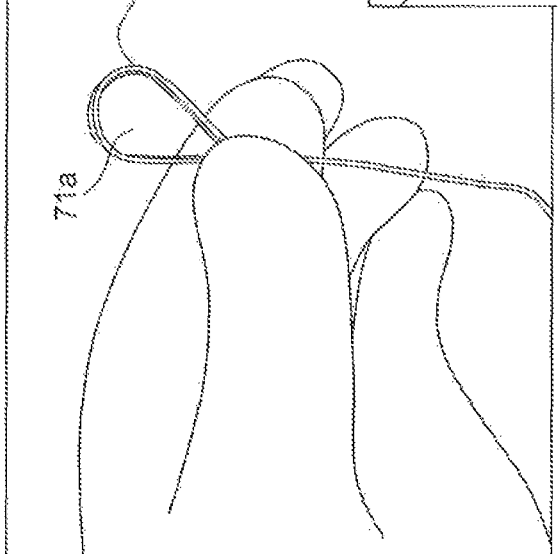

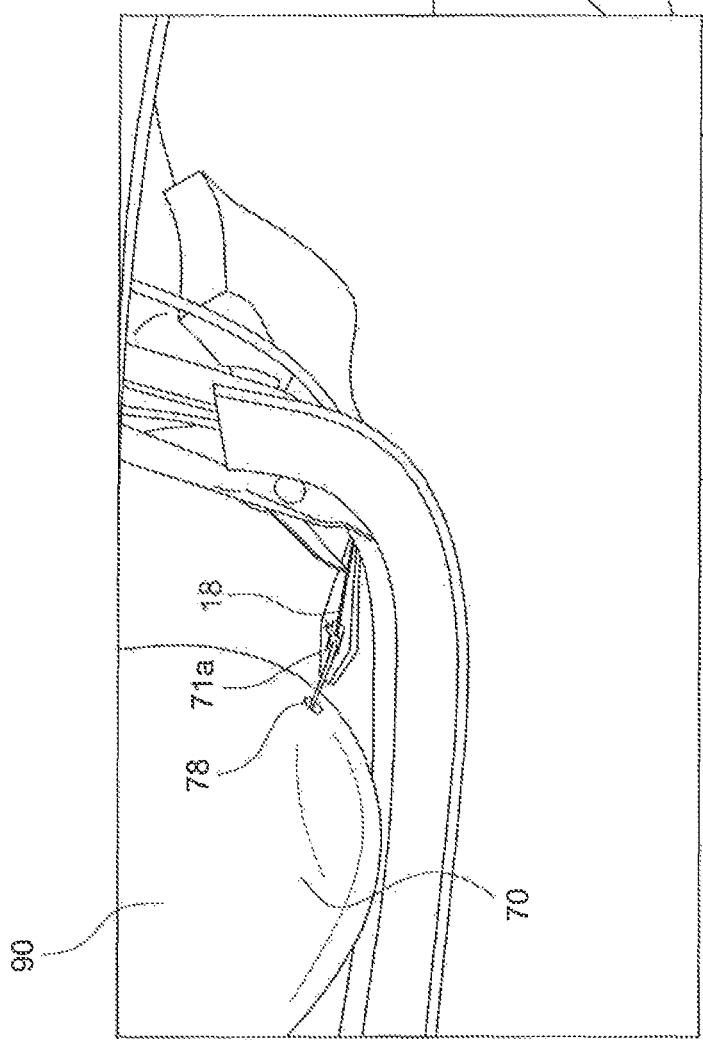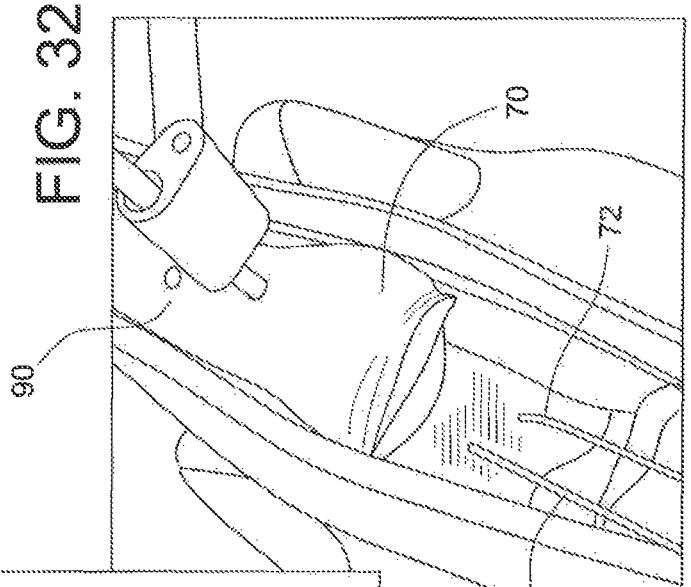

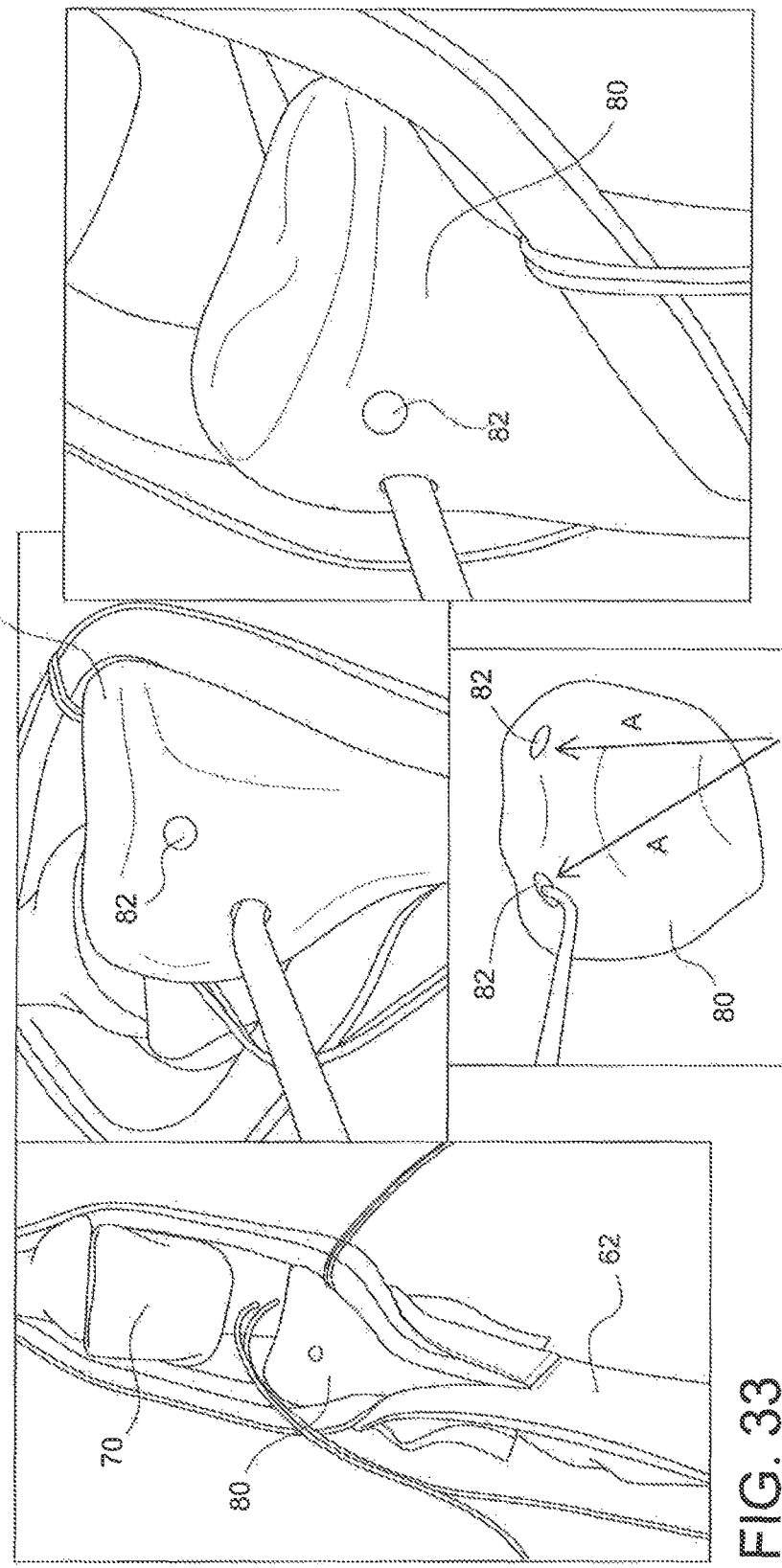

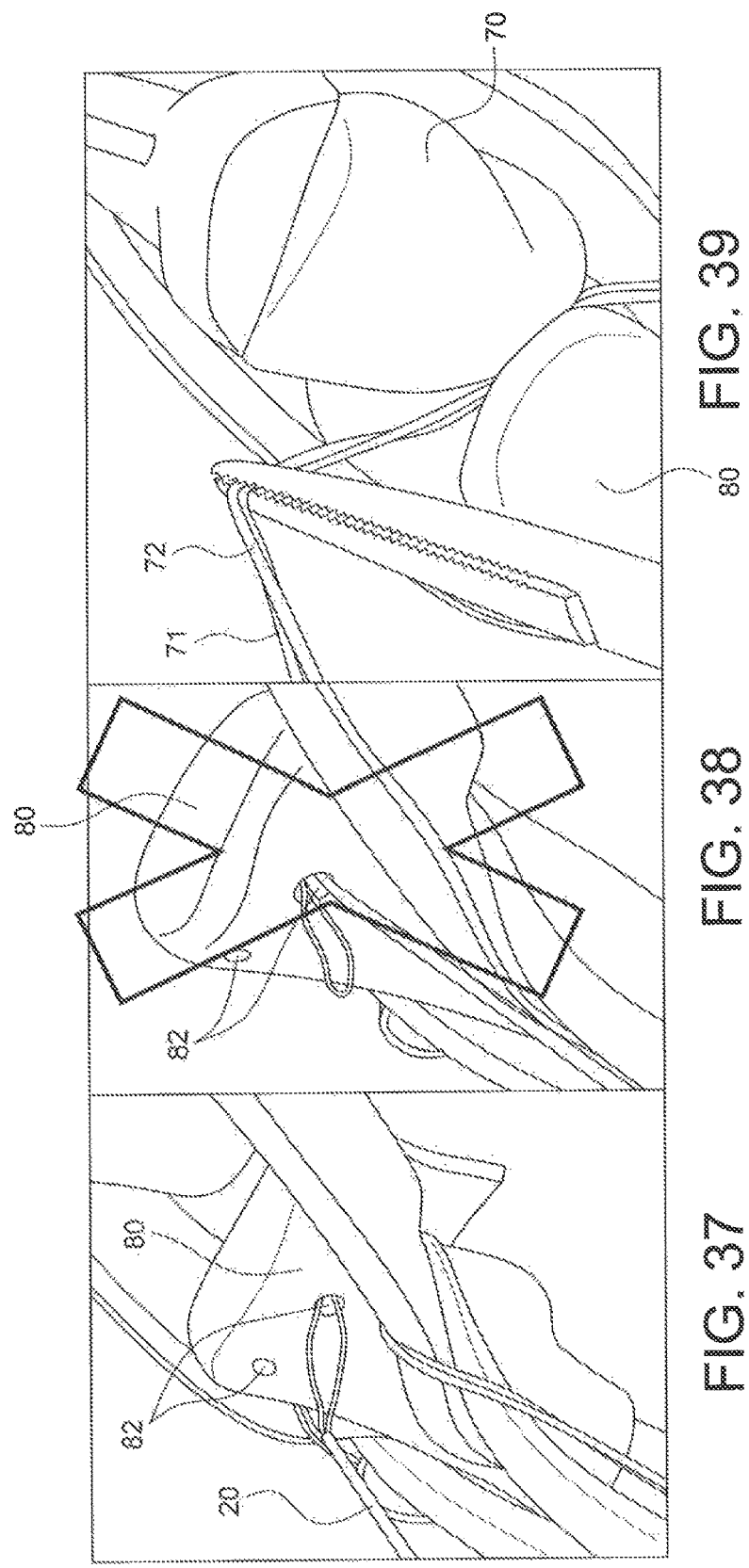

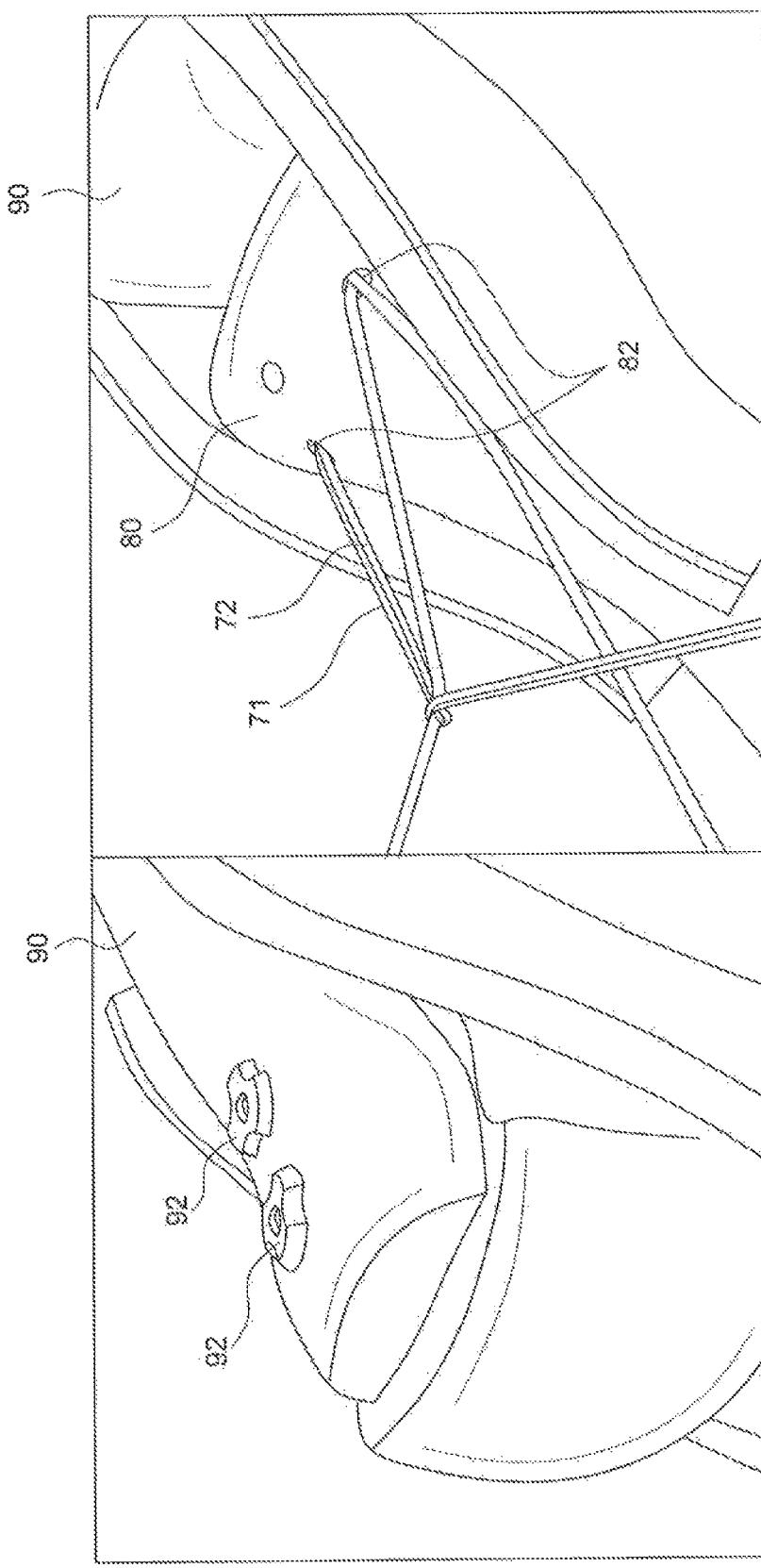

INSTRUMENTS AND METHODS FOR COMPLETE PLANTAR PLATE REPAIRS

CROSS-REFERENCE TO RELATED APPLICATIONS

This is a continuation of U.S. patent application Ser. No. 13/724,600, filed Dec. 21, 2012, which claims the benefit of U.S. Provisional Application No. 61/583,915, filed Jan. 6, 2012, the entire disclosures of which are incorporated by reference herein.

FIELD OF THE INVENTION

The present invention relates to surgical devices and methods, and more particularly, to systems and methods for complete plantar plate repairs.

BACKGROUND OF THE INVENTION

The second metatarsophalangeal (MTP) joint is stabilized by a combination of static resistance provided by the plantar plate and collateral ligaments, and the dynamic pull of the intrinsic flexors. The plantar plate is rectangular to trapezoidal and originates on the metatarsal head through a thin synovial attachment, just proximal to the articular surface, and inserts on the base of the proximal phalanx. Deterioration of the plantar plate often leads to instability of the second MTP joint.

As the principle stabilizer of the MTP joint, the integrity of the plantar plate is essential to stabilize the proximal phalanx of the lesser toes, and its attrition often results in metatarsalgia, plantar swelling, hammertoe deformity, and lesser toe subluxation. Surgical repairs of plantar plate ruptures have evolved with increased appreciation of the anatomy. Primary repairs involve direct visualization of the plantar plate injury and may involve an incision through the plantar of the foot which may lead to complications during healing. Other procedures that address MTP instability include the use of anchors, extensor tendon lengthening, flexor tendon transfers, metatarsal osteotomies and total joint implants, among others.

SUMMARY OF THE INVENTION

The invention provides surgical repair systems and techniques for complete plantar plate repairs. The surgical repair systems and methods of the present invention reconstruct—through a dorsal incision—the plantar plate that leads to the instability of the second MTP joint, restoring the normal alignment of the joint, and minimizing healing complications.

The surgical repair system of the present invention embodies a variety of instruments that provide visualization and access to the plantar plate using suture to complete the repair. The repair system may include some or all of the following instruments: a metatarsal head pusher employed in open surgical space, to move the "capital fragment" in a controlled manner; a suture retriever instrument and a suture retriever funnel (sleeve); a suture passer such as a Mini Scorpion™ DX suture passer and accompanying needle, or a variety of shaped Micro Suture Lasso™ suture passers; a measuring guide; and a small joint distractor. Additional instruments may include drill bits and k-wires as are known for performing surgery. These specialized instruments (i) access an open surgical space and move the "capital fragment" in a controlled/precise manner; (ii) reach into the surgical space and pass suture either by using the Mini Scorpion™ DX suture passer or Micro Suture-Lasso™ suture passers; (iii) pull suture through the bone tunnels enabling reattachment of the plantar plate (ligament) to the bone; and (iv) confer a successfully tensioned plantar plate.

The plantar plate repair method of the present invention comprises inter alia the steps of: (i) intraoperatively demonstrating a plantar plate tear (second metatarsal head is inferior) in the second MTP joint by distraction; (ii) transfixing the plate with a suture passer (mini Scorpion™ DX or micro Suture-Lasso™ suture passers) (just proximal to the tear) and pulling a suture through the plantar plate; (iii) positioning sutures (preferably two sutures with four tails) at the distal aspect of the plantar plate (not yet passed through the phalanx); (iv) passing the suture through the dorsal to plantar drill hole; (v) fixating a metatarsal shortening osteotomy (Weil osteotomy) before tying the sutures; and (vi) tying the sutures with the toe in plantar flexion. At least one of the above-noted steps is conducted with at least one of the instruments of the repair system of the present invention.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 1(a) illustrates a partial cross-sectional view of a Mini Scorpion™ DX suture passer of the present invention employed for plantar plate repair.

FIG. 1(b) is a top view of the Mini Scorpion™ DX suture passer of FIG. 1(a).

FIG. 1(c) is a perceptive view of the Mini Scorpion™ DX suture passer of FIG. 1(a).

FIG. 3(a) illustrates a top view of a Micro Suture-Lasso™ suture passer according to an exemplary embodiment of the present invention (plantar plate pig-tails), and employed for plantar plate repair.

FIG. 3(b) is a lateral view of the Micro Suture-Lasso™ suture passer of FIG. 3(a).

FIG. 3(c) is an enlarged view of detail A of FIG. 3(a).

FIG. 3(d) is a right side view of detail A of FIG. 3(c).

FIG. 4(a) illustrates a top view of a Micro Suture-Lasso™ suture passer according to another exemplary embodiment of the present invention (Micro Suture-Lasso™ suture passer needle), and employed for plantar plate repair.

FIG. 4(b) is a cross-sectional view of the Micro Suture-Lasso™ suture passer of FIG. 4(a).

FIG. 4(c) is an enlarged view of detail G of FIG. 4(b).

FIG. 4(d) is an enlarged view of detail H of FIG. 4(b).

FIG. 4(e) is an enlarged view of detail J of FIG. 4(a).

FIG. 5(a) illustrates a top view of a Micro Suture-Lasso™ suture passer according to another exemplary embodiment of the present invention, and employed for plantar plate repair.

FIG. 5(b) is a lateral view of the Micro Suture-Lasso™ of FIG. 5(a) suture passer.

FIG. 5(c) illustrates a top view of a Micro Suture-Lasso™ suture passer according to another exemplary embodiment of the present invention, and employed for plantar plate repair.

FIG. 5(d) is a lateral view of the Micro Suture-Lasso™ suture passer of FIG. 5(c).

FIG. 6(a) illustrates a top view of a Micro Suture-Lasso™ suture passer according to another exemplary embodiment of the present invention, and employed for plantar plate repair.

FIG. 6(b) is a cross-sectional view of the Micro Suture-Lasso™ suture passer of FIG. 6(a).

FIG. 6(c) is a perspective view of the Micro Suture-Lasso™ suture passer of FIG. 6(a).

FIG. 6(d) is an enlarged view of detail B of FIG. 6(c).

FIG. 6(e) is an enlarged view of detail A of FIG. 6(b).

FIG. 8(a) illustrates a lateral view of a Micro Suture Lasso™ suture passer according to another exemplary embodiment of the present invention, and employed for plantar plate repair.

FIG. 8(b) is an enlarged view of the most distal end of the Micro Suture-Lasso™ suture passer of FIG. 8(a).

FIG. 9(a) illustrates a side view of a Suture Retriever of the present invention employed for plantar plate repair and according to an embodiment of the present invention (with a stopper).

FIG. 9(b) illustrates a side view of a Suture Retriever of the present invention employed for plantar plate repair and according to another embodiment of the present invention (without a stopper).

FIG. 11(a) illustrates a schematic top view of a plantar plate Pusher (which may be reusable or disposable) of the present invention employed for plantar plate repair.

FIG. 11(b) is a side view of the plantar plate Pusher of FIG. 11(a).

FIG. 11(c) is an enlarged view of the distal end of the plantar plate Pusher of FIG. 11(a).

FIG. 11(d) is a left side view of the plantar plate Pusher of FIG. 11(c).

FIG. 11(e) is a cross-sectional view of the plantar plate Pusher of FIG. 11(d), taken along line A-A of FIG. 11(d).

FIGS. 14(a)-(d) illustrate subsequent steps of a method of plantar plate repair according to an embodiment of the present invention.

FIGS. 15(a)-(f) illustrate another series of subsequent steps of a method of complete plantar plate repair according to another embodiment of the present invention.

FIGS. 16(a)-(c) illustrate a series of steps of a plantar plate repair with a suture retriever without a funnel.

FIGS. 17(a)-(c) illustrate a series of steps of a plantar plate repair with a suture retriever with a funnel.

FIGS. 18-42 illustrate another series of steps of a method of complete plantar plate repair according to another embodiment of the present invention.

DETAILED DESCRIPTION OF THE PREFERRED EMBODIMENTS

Figure 2A:
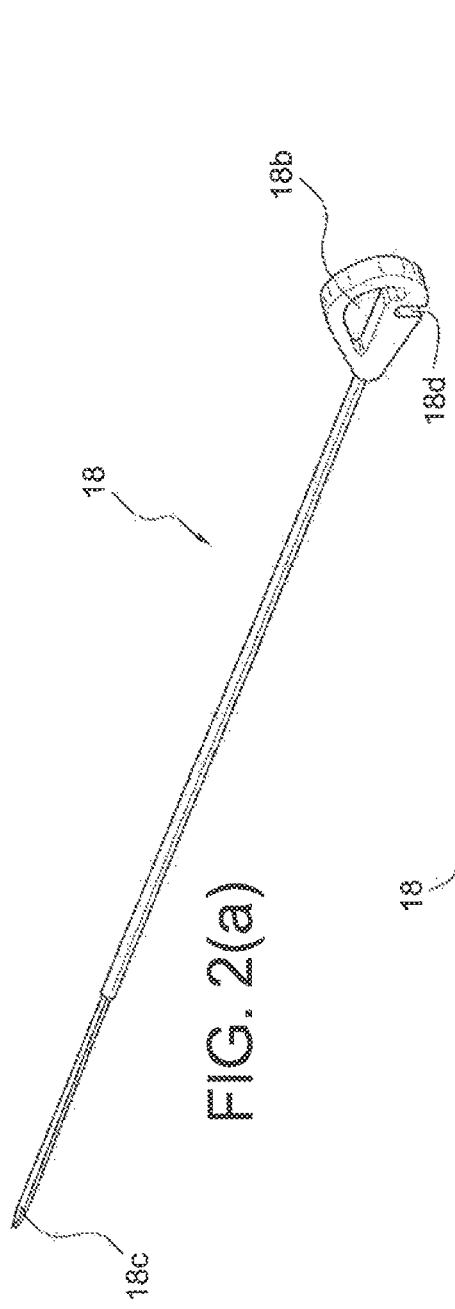
FIG. 2(a) illustrates a perspective view of a Mini Scorpion™ DX suture passer needle with molded handle employed with the Mini Scorpion™ DX of FIG. 1(c).
Figure 2B:
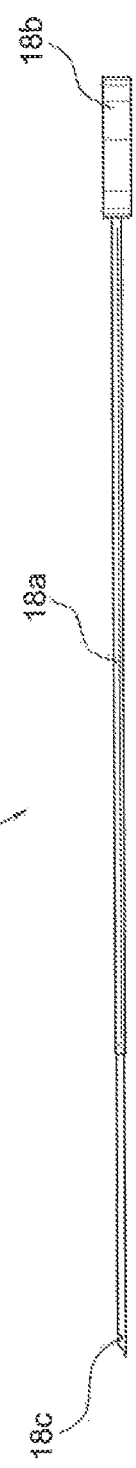
FIG. 2(b) is a top view of the Mini Scorpion™ DX suture passer needle of FIG. 2(a).
Figure 2C:
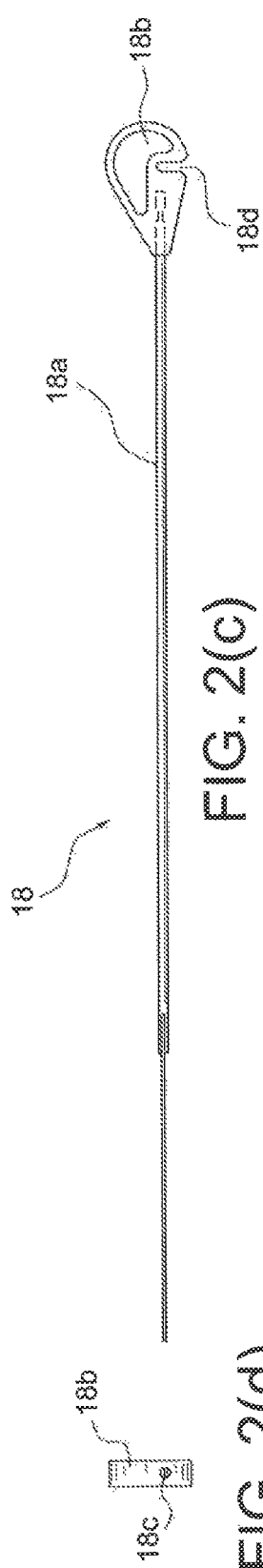
FIG. 2(c) is a partial cross-sectional view of the Mini Scorpion™ DX suture passer needle of FIG. 2(a).
Figure 2D:
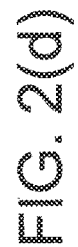
FIG. 2(d) is a left side view of the Mini Scorpion™ DX suture passer needle of FIG. 2(c).

The present invention provides systems and methods for plantar plate repair. The systems of the present invention include surgical instruments that confer enhanced repair (a tensioned plantar plate), while decreasing the chance of wound complications and plantar tissue trauma.

An exemplary method of plantar plate repair employing a dorsal approach and combining a Weil osteotomy in accordance with the present invention comprises inter alia the steps of: Weil osteotomy is performed allowing the capital fragment to be recessed under the metatarsal; digital distraction is obtained using a distraction clamp over K-wires; the plantar plate is assessed and repaired using suture (with a novel suture passing hand instrument known as the Mini Scorpion™ DX suture passer—this device allows the surgeon to pass suture through the plantar plate); the plantar plate is repaired back to the proximal phalanx. According to this method (the Complete Plantar Plate Repair or the CPR method), surgeons now have the option to repair the primary pathology, the plantar plate itself, using a dorsal approach.

Referring now to the drawings, where like elements are designated by like reference numerals, FIGS. 1-13 illustrate surgical instruments of the system of the present invention employed during a method of plantar plate repair. FIGS. 14-42 illustrate exemplary steps of methods of plantar plate repair 100 with the instruments of FIGS. 1-13.

FIGS. 1(a)-(c) illustrate various views of a Mini Scorpion™ DX 10 employed for a plantar plate repair according to an embodiment of the present invention. The Mini Scorpion™ DX 10 includes the following components/features: Mini Scorpion™ DX tip-tube 1; Mini Scorpion™ DX actuator 2; Scorpion link 3; cutter tip 4 (for example, a 4.2 mm standard cutter tip 4); Mini Scorpion™ DX jaw 5; Scorpion Fastpass trap door 6; Scorpion Fastpass trap door spring 7; tip pin 8 (for example, a 4.5 mm tip pin 8); Scorpion thumb 9; Scorpion palm 10a; Scorpion stop arm 11; Scorpion spring rod 12; Scorpion handle spring 13; reverse punch set screw 14; Scorpion finger 15; Scorpion finger spring 16; and Scorpion handle pin 17.

FIGS. 2(a)-(d) illustrate various views of a Mini Scorpion™ DX needle 18 with an exemplary nitinol welded tube 18a and an exemplary molded handle 18b (with a handle notch 18d) employed with the Mini Scorpion™ DX 10 of FIGS. 1(a)-(c). Mini Scorpion™ DX needle 18 is also provided with a suture notch 18c at its most distal end. FIG. 2(a) shows the instrument 18 with the suture notch 18c on right and the handle notch 18d on the bottom. The Mini Scorpion™ DX 10 and needle 18 function well to pass a mattress stitch in the plantar plate, particularly in tight spaces.

Figure 7A:
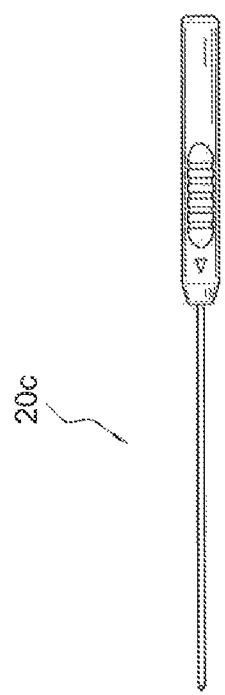
FIG. 7(a) illustrates a top view of a Micro Suture-Lasso™ suture passer according to another exemplary embodiment of the present invention, and employed for plantar plate repair.
Figure 7B:
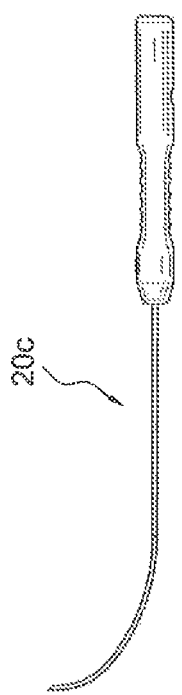
FIG. 7(b) is a lateral view of the Micro Suture-Lasso™ passer of FIG. 7(a).
Figure 7C:
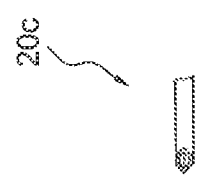
FIG. 7(c) is an enlarged view of the most distal end of the Micro Suture-Lasso™ suture passer of FIG. 7(a).

FIGS. 3(a)-(d) illustrate various views of Micro Suture-Lasso™ suture passer 20 according to an exemplary embodiment of the present invention. FIGS. 4(a)-(e) illustrate various views of Micro Suture-Lasso™ 22 suture passers according to another exemplary embodiment of the present invention. FIGS. 5(a)-(d) illustrate various views of Micro Suture-Lasso™ suture passers 20a, 20a' according to yet other exemplary embodiments of the present invention (with different curvatures of the distal shaft of the instrument). FIGS. 6(a)-(e) illustrate various views of Micro Suture-Lasso™ suture passer 20b according to another exemplary embodiment of the present invention. FIGS. 7(a)-(c) illustrate various views of Micro Suture-Lasso™ suture passer 20c according to another exemplary embodiment of the present invention. FIGS. 8(a)-(b) illustrate various views of Micro Suture-Lasso™ suture passer 20d according to another exemplary embodiment of Lassos 20a, 20b, 20c, 20d, 22 are particularly useful in small-size patients and pass a mattress stitch more proximally in the plantar plate.

FIG. 9(a) illustrates a side view of a Suture Retriever 30 provided with loop 31 (a Nitinol loop 31) and with stopper 33. FIG. 9(b) illustrates a side view of a Suture Retriever 30a provided without stopper 33. Both instruments may be employed for the plantar plate repair of the present invention and are provided with Nitinol loop 31 to pull a flexible strand (for example, suture) through the bone tunnels.

Figure 10A:
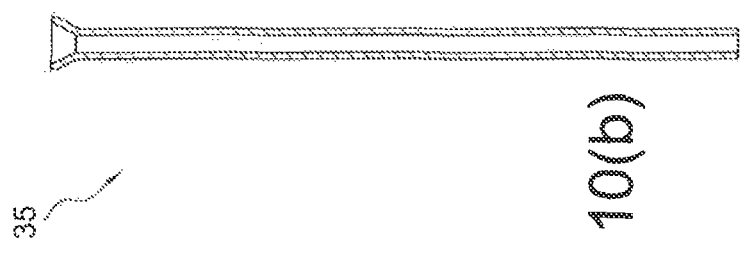
FIG. 10(a) illustrates a frontal view of a Suture Retriever funnel (sleeve) employed with the Suture Retrieval of FIGS. 9(a) and 9(b).
Figure 10B:
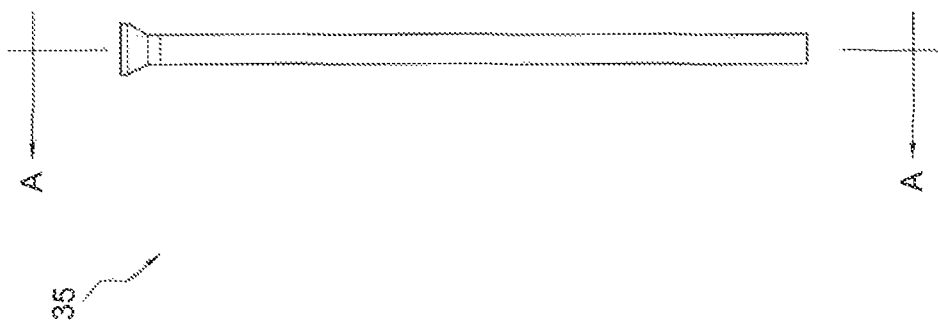
FIG. 10(b) is a cross-sectional view of the Suture Retriever funnel (sleeve) of FIG. 10(a), taken along line A-A of FIG. 10(a).

FIGS. 10(a)-(b) illustrate an exemplary funnel 35 (sleeve 35) employed with the Suture Retriever of FIGS. 9(a)-(b). The Suture Retriever 30, 30a and funnel 35 pass suture 71, 72 through the phalanx 80. Steps for a plantar plate repair with a suture retriever without a funnel 35 (sleeve 35) are illustrated in FIGS. 16(a)-(c) which show how the Nitinol loop 31 cannot be pushed and how the loop doubles back and drags behind (on the plantar side, the wire must extend the length of the loop in order for it to be released). Steps for a plantar plate repair with a suture retriever with a funnel 35 (sleeve 35) of the present invention are illustrated in FIGS. 17(a)-(c) which show a funnel 35 of only about 1.5 inches long (to fit in a 1.1 or 1.6 mm K-wire hole). The smooth and flexible plastic sleeve 35 can be preloaded on the retriever or placed free-hand. The sleeve 35 can slide up the retriever (in situ).

FIGS. 11(a)-(e) illustrate various views of a plantar plate Pusher 40 which may be reusable or disposable and which may be employed to slide the capital fragment back.

Figure 12A:
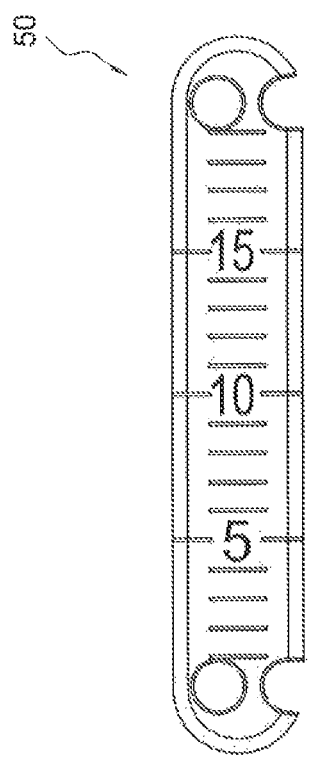
FIG. 12(a) illustrates a schematic top view of a plantar plate Measuring Guide (which may be disposable) of the present invention employed for plantar plate repair.
Figure 12B:
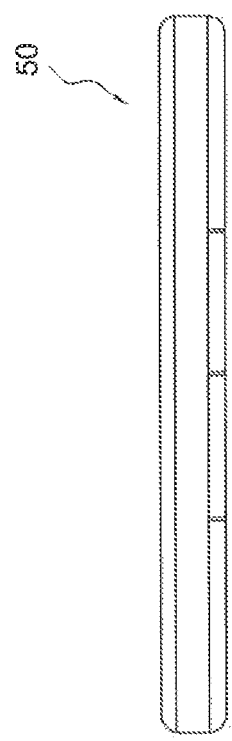
FIG. 12(b) is a side view of the plantar plate Measuring Guide of FIG. 12(a).

FIGS. 12(a)-(b) illustrate a plantar plate Measuring Guide 50 which is preferably disposable.

Figure 13:
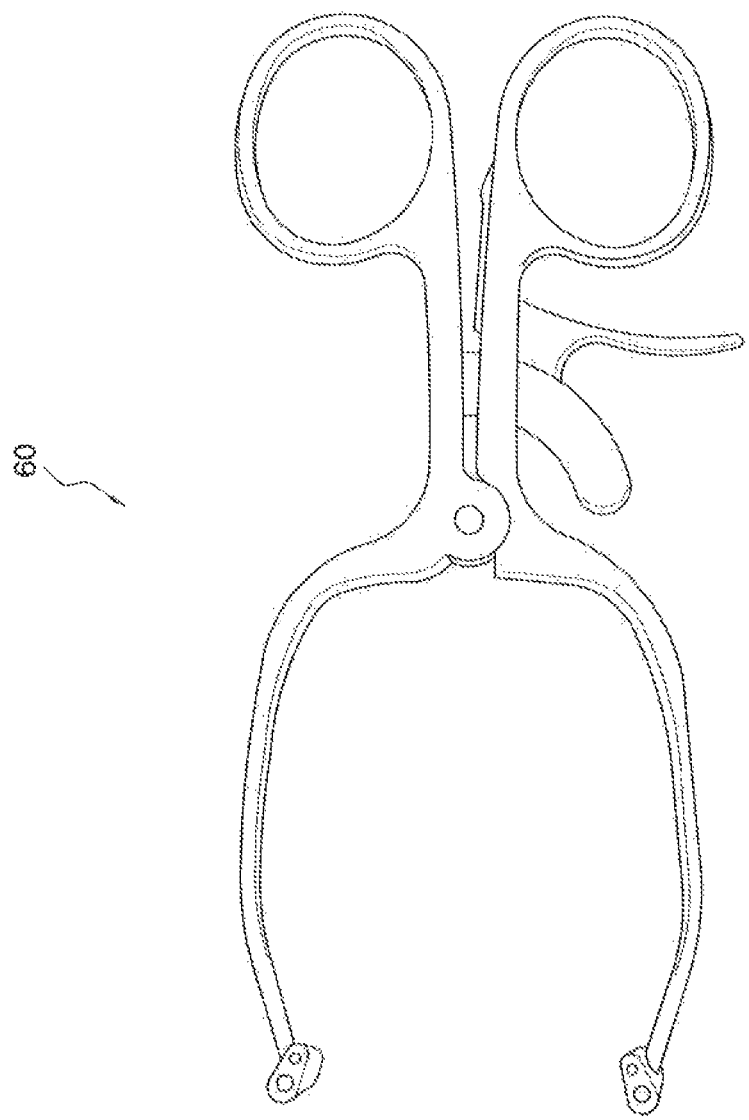
FIG. 13 illustrates a plantar plate Distractor of the present invention employed for plantar plate repair.

FIG. 13 illustrates a plantar plate Distractor 60 (small joint Distractor 60).

The repair system of the present invention includes at least one of the following instruments:
a metatarsal head pusher (such as plantar plate pusher 40) employed in open surgical space, to move the "capital fragment" in a controlled manner; this pusher has a specifically-designed head to prevent damage to the articular cartilage while pushing the fragment;
a measuring guide (such as plantar plate measuring guide 50);
a plantar plate distractor (such as plantar plate distractor 60)—designed to work with k-wires to distract the joint;
k-wires to work with the plantar plate distractor;
flexible strands such as sutures—for example, FiberWire® suture 71, 72;
a suture passer such as a Mini Scorpion™ DX 10 and accompanying needle 18, or a set of Micro Suture Lassos™ 20, 20a, 20a', 20b, 20c, 20d, 22;
a suture retriever instrument (such as suture retriever 30, 30a)—Nitinol loop 31 to pull the suture 71, 72 through the bone tunnels; and
a suture retriever sleeve or funnel (such as suture retrieval funnel 35)—if used, this instrument ensures that the nitinol loop 31 on the suture retriever 30, 30a does not loop back.

FIGS. 14(a)-(d) illustrate subsequent steps of a method of plantar plate repair according to an embodiment of the present invention, illustrating suture passer 10 (Mini Scorpion™ DX 10) and accompanying needle 18 and plantar plate distractor 60.

FIGS. 15(a)-(f) illustrate another series of subsequent steps of a method of complete plantar plate repair according to an embodiment of the present invention:

FIG. 15(a): intraoperative demonstration of distraction of the second MTP joint 99 with a plantar plate tear 77 (second metatarsal head 90 is inferior);

FIG. 15(b): a suture passer transfixing the plantar plate 70 (just proximal to the tear 77) and helping to pull the flexible strand 71, 72 (for example, suture) through the plantar plate 70;

FIG. 15(c): two flexible strands 71, 72 (for example, two sutures 71, 72) positioned at the distal aspect of the plantar plate (not yet passed through the phalanx);

FIG. 15(d): passing the flexible strands 71, 72 (sutures 71, 72) through the dorsal to plantar drill hole;

FIG. 15(e): fixation of metatarsal shortening (Weil) osteotomy before tying the flexible strands 71, 72 (sutures 71, 72); and FIG. 15(f): tying the flexible strands 71, 72 (sutures 71, 72) with the toe in plantar flexion to form knots 71a, 72a of final repair 100a.

An exemplary surgical technique for a plantar plate repair with the instrument system of the present invention follows the exemplary steps below:

1. A dorsal longitudinal incision is centered over the second web space. A longitudinal capsulotomy is performed just inferior to the tendons of the extensor digitorum longus and brevis to expose the affected second MTP joint 99.

2. A partial collateral ligament release off of the proximal phalanx 80 of the MTP joint 99 improves visualization.

3. A metatarsal shortening osteotomy (Weil osteotomy) is performed using a sagittal saw. The saw cut is made parallel to the plantar aspect of the foot, starting at a point 2 to 3 mm below the top of the metatarsal articular surface. The capital fragment is provisionally pushed proximally about 10 mm and fixed with a temporary vertical Kirschner wire (k-wire), to hold it in a retracted position.

4. A second vertical Kirschner wire is then placed in the base of the proximal phalanx. A special plantar plate distractor 60 is placed over the vertical wires and spread to expose the plantar plate 70.

5. The plantar plate tear 77 is evaluated and graded. Longitudinal tears in the plate (grade 3) are repaired with a side-to-side interrupted suture (for example, a 0-Fiber-Wire®). Distal transverse tears (grades 1 and 2) are repaired by placing the same suture in the distal plantar plate. The distal plantar edge of the proximal phalanx is roughened with a burr or curette to prepare a surface for reimplantation of the plantar plate. The distal plantar plate is transfixed just proximal to the transverse tear using a small curved needle or a special curved Micro Suture Lasso™ suture passer such as, for example, Micro Suture-Lasso™ suture passer 20 of FIGS. 3(a)-(d), or a suture passing instrument such as, for example, Mini Scorpion™ DX suture passer 10 of FIGS. 1(a)-(c) to pass the flexible strand 71, 72 (suture 71, 72) within the restricted MTP joint surgical area of exposure.

6. Using a 1.6-mm drill or k-wire, two parallel drill holes are created medially and laterally on the proximal phalanx 80, directed from the dorsal cortex of the proximal phalanx to the plantar rim of the proximal phalanx. This permits passing of a suture, plantar to dorsal, to fix the plantar plate 70 to its insertion point at the plantar base of the phalanx 80.

7. The metatarsal shortening (Weil) osteotomy is then reduced (to surgeon's desired position). It is fixed in optimal position with one or two small screws or k-wire.

8. The toe is held reduced on the metatarsal articular surface, in plantar flexion, and with tension on the sutures 71, 72 (having been pulled through the holes in the proximal phalanx 80). They are tied over the dorsal phalangeal cortex, thus advancing the plantar plate onto the base of the proximal phalanx.

9. A lateral soft tissue reefing to repair the lateral collateral ligamentous release is performed with nonabsorbable sutures.

10. An interrupted wound closure is performed. The foot is placed in tape compression dressing with the digit held in 10° to 15° of plantar flexion.

Figure 19:
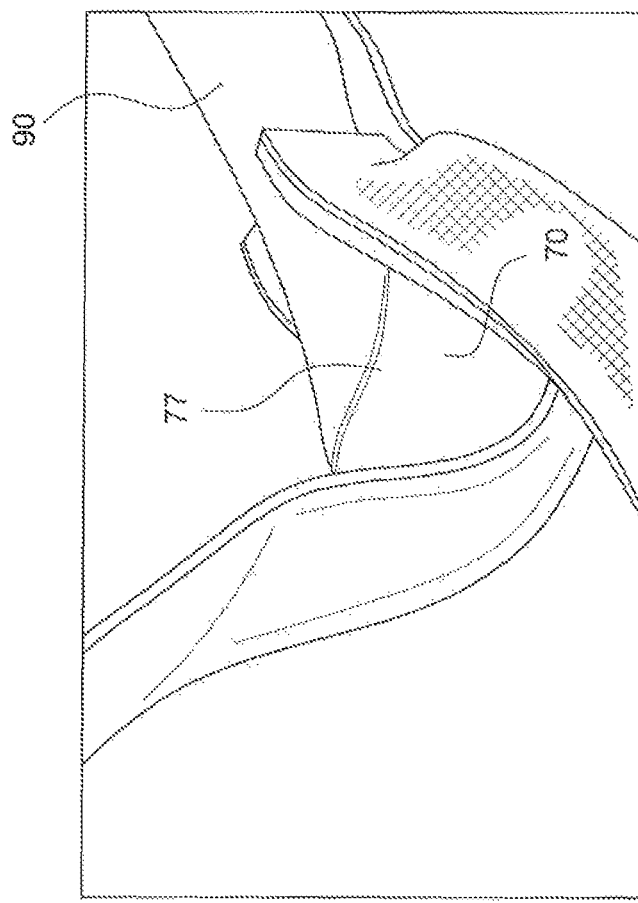
Figure 18:
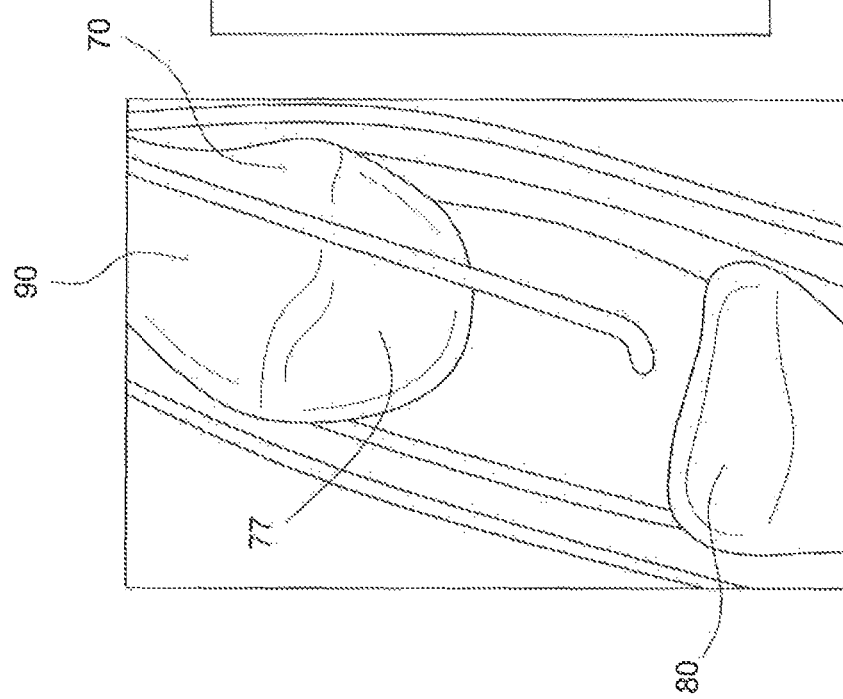

FIGS. 18-42 illustrate the steps of a plantar plate repair with the instruments of the present invention in accordance with another embodiment of the invention:

FIGS. 18 and 19: The tear 77 is visualized; if more than 40% is torn, detach the plantar plate 70 from the rim of the proximal phalanx 80 (an elevator may be optionally used).

FIGS. 20-23: A metatarsal shortening osteotomy is performed with osteotome 75. Use the metatarsal pusher 40 to push the plantar fragment between 8-10 mm away from the joint 99 and provisionally fixate with 1.6 mm threaded or non-threaded k-wire 76.

FIGS. 24 and 25: Optionally, based on pre-operative measurements, a template can be used to cut the dorsal shelf of the metatarsal to a specific length using a bone cutter. This will allow better visualization and access to the plantar plate 70.

FIGS. 26-28: A unique plantar plate distractor 60 with 1.6 or 2.0 mm threaded or non-threaded k-wires is then placed in the phalanx 80 and the metatarsal 90 and distracts the joint 99.

FIGS. 29 and 30: Create a noose 71a at the end of the flexible strand 71 (#0 FiberWire® suture 71) and load it into the Mini Scorpion™ DX suture passer 10.

FIGS. 31 and 32: Fire the needle 18 medial and lateral, creating an inverted mattress stitch 78 in the plantar plate 70. The step is repeated for two independent sutures 71, 72 in the plantar plate 70.

FIGS. 33-36: Remove the distractor 60 and use a towel clamp 62 to plantar flex the phalanx 80. Two crossing drill holes 82 using a 1.6 mm k-wire 82 are made in the proximal phalanx 80. This allows passing a suture 71, 72 plantar to dorsal, to fix the plantar plate 70 to its insertion point at the plantar base of the phalanx 80. The k-wire exits the phalanx just below the cartilage (arrows A of FIG. 35). This allows for easier suture passing.

FIGS. 37-39: Pass the sutures 71, 72 using the Micro Suture-Lasso™ suture passer 20. The suture passer must not flip back on itself when passing in the hole. A mosquito may be used to aid in the passing of the sutures 71, 72 into the suture passer.

FIGS. 40 and 41: Weil osteotomy is then fixed in optimal position with one or two fixation devices 92 (such as 2.0 mm Quickfix screws 92 or any screw or pin). The toe is held in the optimal position and both sets of suture ends 71, 72 are tied over the phalanx 80 forming knots 71a, 72a (FIG. 42).

Figure 42:
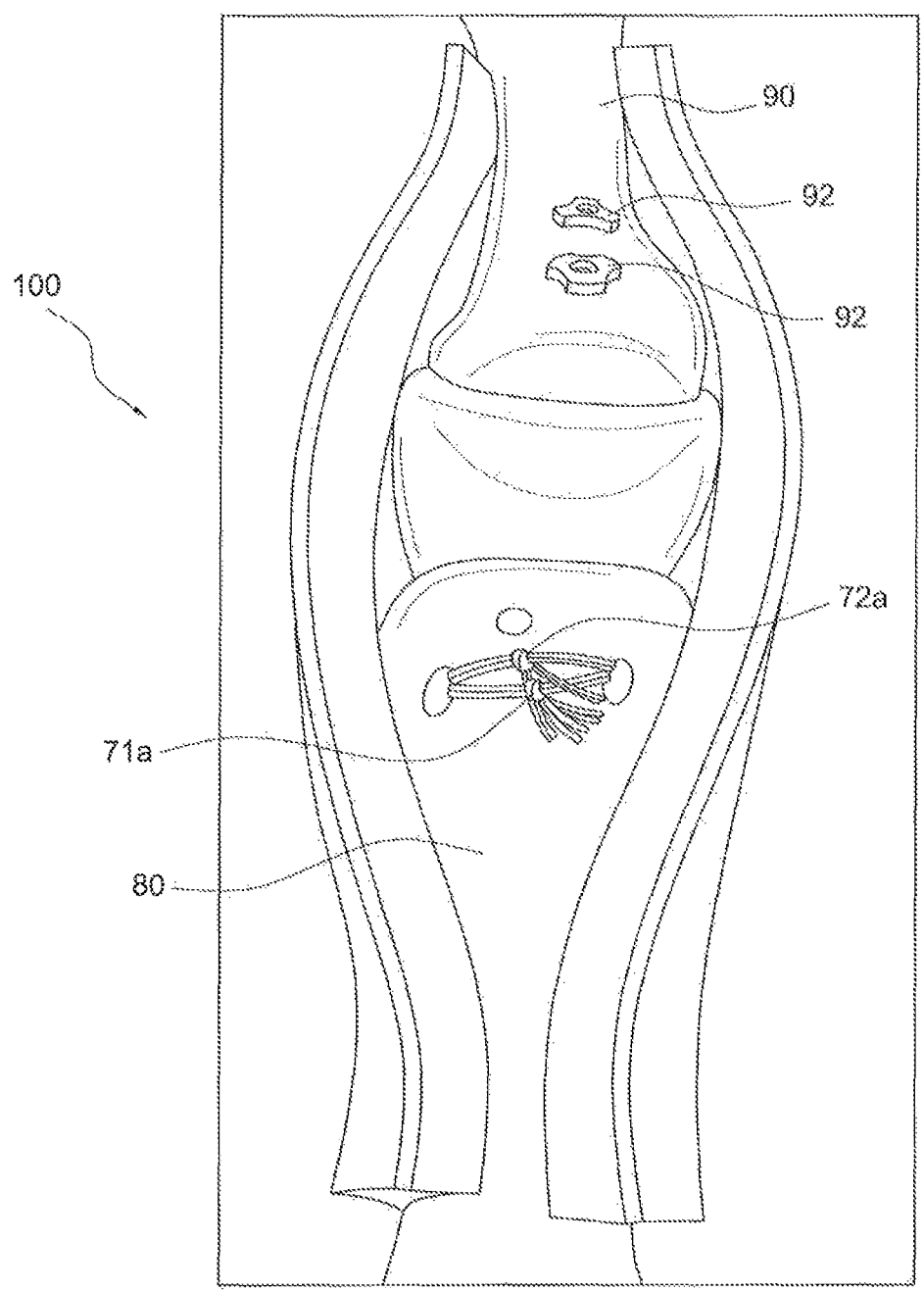

FIG. 42 shows the final repair 100.

The flexible strands 71, 72 may be made of any known suture material, such as ultrahigh molecular weight polyethylene (UHMWPE) or the FiberWire® suture (disclosed in U.S. Pat. No. 6,716,234 which is hereby incorporated by reference in its entirety).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of plantar plate repair, comprising:
performing a longitudinal incision to expose a metatarsophalangeal joint;
distracting the metatarsophalangeal joint to expose a plantar plate, wherein distracting the metatarsophalangeal joint includes placing a first k-wire in a metatarsal bone of the metatarsophalangeal joint, placing a second k-wire in a phalangeal bone of the metatarsophalangeal joint, placing a distractor over the first k-wire and the second k-wire, and then spreading the distractor to expose the plantar plate; wherein placing the distractor over the first k-wire and the second k-wire includes moving the distractor down over the first k-wire and the second k-wire until the distractor abuts both the metatarsal bone and the phalangeal bone; roughening a surface of the phalangeal bone to prepare the surface for reattachment of the plantar plate; passing a suture through the plantar plate; removing the distractor, the first k-wire, and the second k-wire; drilling a hole through the phalangeal bone; passing the suture through the hole; and tying a knot in the suture to complete the plantar plate repair;
wherein the distractor includes a first handle, a first arm that extends from the first handle, a second handle, a second arm that extends from the second handle, and a pivot pin extending through the first arm and the second arm; wherein each of the first handle and the second handle includes an oblong shaped finger opening disposed at a proximal most end of the distractor.

2. The method as recited in claim 1, comprising dissecting a portion of a collateral ligament of the metatarsophalangeal joint to improve visualization of the plantar plate before passing the suture through the plantar plate.

3. The method as recited in claim 2, wherein at least a portion of the collateral ligament is released off of the phalangeal bone.

4. The method as recited in claim 2, comprising repairing the collateral ligament with a second suture.

5. The method as recited in claim 1, wherein distracting the metatarsophalangeal joint includes locating distal portions of the distractor over the first k-wire and the second k-wire, and then spreading the distal portions of the distractor apart to move the metatarsal bone and the phalangeal bone apart from one another, thereby exposing the plantar plate.

6. The method as recited in claim 1, wherein the first k-wire and the second k-wire are 1.6 mm or 2.0 mm k-wires.

7. The method as recited in claim 1, wherein the suture is made of ultrahigh molecular weight polyethylene.

8. The method as recited in claim 1, wherein drilling the hole through the phalangeal bone includes drilling a third k-wire through the phalangeal bone.

9. The method as recited in claim 8, wherein the third k-wire is drilled in a dorsal to plantar direction.

10. The method as recited in claim 1, wherein passing the suture through the hole includes passing the suture in a plantar to dorsal direction.

11. The method as recited in claim 1, wherein tying the knot includes tying the knot near a dorsal phalangeal cortex of the phalangeal bone.

12. The method as recited in claim 1, wherein passing the suture through the plantar plate includes forming a stitch in the plantar plate.

13. The method as recited in claim 1, wherein each of the first arm and the second arm includes a housing having a proximal passage and a distal passage, and at least one of the proximal passage and the distal passage is sized to accommodate the first k-wire or the second k-wire.

14. The method as recited in claim 13, wherein the housing is disposed at a distal most end of the first arm and is enlarged relative to the first arm.

15. The method as recited in claim 13, wherein the proximal passage includes a first diameter and the distal passage includes a second diameter that is larger than the first diameter.

16. A method of plantar plate repair, comprising:
performing a longitudinal incision to expose a metatarsophalangeal joint; distracting the metatarsophalangeal joint to expose a plantar plate, wherein distracting the metatarsophalangeal joint includes placing a first k-wire in a metatarsal bone of the metatarsophalangeal joint, placing a second k-wire in a phalangeal bone of the metatarsophalangeal joint, placing a distractor over the first k-wire and the second k-wire, and then spreading the distractor to expose the plantar plate;
wherein the distractor includes a first handle, a first arm that extends from the first handle, a second handle, and a second arm that extends from the second handle, wherein each of the first handle and the second handle includes an oblong shaped finger opening disposed at a proximal most end of the distractor and a pivot pin extending through the first arm and the second arm and each of the first arm and the second arm includes a housing that is enlarged relative to the first arm and the second arm, each housing including a proximal passage and a distal passage, and at least one of the proximal passage and the distal passage is sized to accommodate the first k-wire or the second k-wire, and wherein the distal passage includes a larger diameter than the proximal passage;
wherein placing the distractor over the first k-wire and the second k-wire includes inserting the first k-wire and the second k-wire through either the proximal passage or the distal passage of one of the housings such that the first k-wire and the second k-wire enter first through bottom surfaces of the housings and then exit through top surfaces of the housings; passing a suture through the plantar plate; removing the distractor, the first k-wire, and the second k-wire; drilling a hole through the phalangeal bone; passing the suture through the hole; and tying a knot in the suture to complete the plantar plate repair.

* * * * *